US010919034B2

United States Patent
U'ren et al.

(10) Patent No.: US 10,919,034 B2
(45) Date of Patent: Feb. 16, 2021

(54) APPARATUS, SYSTEM, AND METHOD FOR COLLECTING A TARGET MATERIAL

(71) Applicant: RareCyte, Inc., Seattle, WA (US)

(72) Inventors: Lance U'ren, Seattle, WA (US); Ronald Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 214 days.

(21) Appl. No.: 15/942,182

(22) Filed: Mar. 30, 2018

(65) Prior Publication Data

US 2018/0221869 A1  Aug. 9, 2018

Related U.S. Application Data

(63) Continuation of application No. 15/264,257, filed on Sep. 13, 2016, now Pat. No. 9,956,555, which is a (Continued)

(51) Int. Cl.
*B01L 3/00* (2006.01)
*B01L 9/00* (2006.01)
(Continued)

(52) U.S. Cl.
CPC .......... *B01L 3/50215* (2013.01); *B01D 21/26* (2013.01); *B01L 3/5021* (2013.01); *B01L 3/5635* (2013.01); *G01N 1/4077* (2013.01); *G01N 33/491* (2013.01); *B01D 21/262* (2013.01); *B01L 9/50* (2013.01);
(Continued)

(58) Field of Classification Search
CPC . B01D 21/26; B01D 21/262; B01L 2200/026; B01L 2200/0652; B01L 2200/0673; B01L 2300/0672; B01L 2300/0848; B01L 2300/0851; B01L 2400/0409; B01L 2400/0683; B01L 3/5021; B01L 3/50215; B01L 3/5635; B01L 9/50;
(Continued)

(56) References Cited

U.S. PATENT DOCUMENTS 3,661,265 A   5/1972  Greenspan
3,771,965 A  11/1973  Grams
(Continued)

FOREIGN PATENT DOCUMENTS

JP    2005514987 A    5/2005
WO   WO1997012681 A1  4/1997
WO   WO2013070252     5/2013

OTHER PUBLICATIONS

Greiner Bio-One; CicoQuick, Instruction Manual; 8 pages; retrieved from the Internet (https://www.gbo.com/fileadmin/user_uoload/999999_UserGuide_OncoQuick_E.pdf) on May 22, 2018.

*Primary Examiner* — Jennifer Wecker
(74) *Attorney, Agent, or Firm* — Shay Glenn LLP

(57) ABSTRACT

This disclosure is directed to an apparatus, system and method for retrieving target material from a suspension. A system includes a processing vessel, a displacement fluid, and a tube. The tube includes a funnel, a cannula, and a cavity. The cannula allows for fluid communication between the funnel and the cavity, such that the processing vessel is inserted into the cavity, and the cannula extends into the processing vessel.

15 Claims, 21 Drawing Sheets

Related U.S. Application Data continuation-in-part of application No. 14/610,522, filed on Jan. 30, 2015, now Pat. No. 9,539,570, and a continuation-in-part of application No. 14/495,449, filed on Sep. 24, 2014, now Pat. No. 9,039,999, which is a continuation-in-part of application No. 14/090,337, filed on Nov. 26, 2013, now abandoned, and a continuation-in-part of application No. 14/266,939, filed on Aug. 26, 2013, now abandoned.

(60) Provisional application No. 62/345,172, filed on Jun. 3, 2016, provisional application No. 61/935,457, filed on Feb. 4, 2014, provisional application No. 61/732,029, filed on Nov. 30, 2012, provisional application No. 61/745,094, filed on Dec. 21, 2012, provisional application No. 61/791,883, filed on Mar. 15, 2013, provisional application No. 61/818,301, filed on May 1, 2013, provisional application No. 61/869,866, filed on Aug. 26, 2013.

(51) Int. Cl.
*G01N 1/40* (2006.01)
*G01N 33/49* (2006.01)
*B01D 21/26* (2006.01)

(52) U.S. Cl.
CPC . *B01L 2200/026* (2013.01); *B01L 2200/0652* (2013.01); *B01L 2200/0673* (2013.01); *B01L 2300/0672* (2013.01); *B01L 2300/0848* (2013.01); *B01L 2300/0851* (2013.01); *B01L 2400/0409* (2013.01); *B01L 2400/0683* (2013.01); *G01N 2001/4083* (2013.01); *Y10T 436/25375* (2015.01)

(58) Field of Classification Search
CPC ......... G01N 1/4077; G01N 2001/4083; G01N 33/491; Y10T 436/25375
See application file for complete search history.

(56) References Cited

U.S. PATENT DOCUMENTS

| | | | |
|---|---|---|---|
| 3,814,248 A | 6/1974 | Lawhead | |
| 3,873,271 A | 3/1975 | Young et al. | |
| 3,879,295 A | 4/1975 | Glover et al. | |
| 4,037,464 A | 7/1977 | Werander | |
| 4,187,861 A | 2/1980 | Heffernan | |
| 4,436,631 A | 3/1984 | Graham, Jr. et al. | |
| 4,464,254 A | 8/1984 | Dojki et al. | |
| 4,644,807 A | 2/1987 | Mar | |
| 4,925,627 A | 5/1990 | Johnson | |
| 4,927,605 A | 5/1990 | Dorn et al. | |
| 5,019,243 A | 5/1991 | Ewen et al. | |
| 5,030,341 A | 7/1991 | McEwen et al. | |
| 5,248,480 A | 9/1993 | Greenfield et al. | |
| 5,254,312 A | 10/1993 | Steebler et al. | |
| 5,282,981 A * | 2/1994 | Adams | B01L 3/50215 210/516 |
| 5,286,453 A | 2/1994 | Pope | |
| 5,393,674 A | 2/1995 | Levine et al. | |
| 5,560,830 A | 10/1996 | Coleman et al. | |
| 5,646,004 A * | 7/1997 | Van Vlasselaer | C12N 5/0093 435/7.25 |
| 5,714,125 A | 2/1998 | Sagstetter | |
| 5,888,831 A | 3/1999 | Gautsch | |
| 5,910,289 A | 6/1999 | Sagstetter | |
| 6,221,655 B1 | 4/2001 | Fung et al. | |
| 6,401,552 B1 * | 6/2002 | Elkins | B01L 3/5021 422/548 |
| 6,479,298 B1 | 11/2002 | Miller et al. | |
| 7,323,304 B2 | 1/2008 | Dahm | |
| 7,456,024 B2 | 11/2008 | Dahm et al. | |
| 7,524,641 B2 | 4/2009 | Jurgensen et al. | |
| 7,959,866 B2 | 6/2011 | Crawford et al. | |
| 9,039,999 B2 | 5/2015 | Campton et al. | |
| 9,217,697 B2 | 12/2015 | U'ren et al. | |
| 9,513,291 B2 | 12/2016 | Campton et al. | |
| 9,539,570 B2 | 1/2017 | U'ren et al. | |
| 9,625,360 B2 | 4/2017 | U'Ren et al. | |
| 9,945,839 B2 | 4/2018 | Campton et al. | |
| 9,956,555 B2 | 5/2018 | U'ren et al. | |
| 2001/0031688 A1 | 10/2001 | Anderson | |
| 2002/0169408 A1 | 11/2002 | Beretta et al. | |
| 2003/0208162 A1 | 11/2003 | Crawford | |
| 2004/0025603 A1 | 2/2004 | Liseo et al. | |
| 2004/0025935 A1 | 2/2004 | Liseo et al. | |
| 2008/0025877 A1 | 1/2008 | Alley | |
| 2008/0284164 A1 | 11/2008 | Kerin et al. | |
| 2009/0100915 A1 | 4/2009 | Shiraki et al. | |
| 2010/0093551 A1 | 4/2010 | Montagu | |
| 2010/0120596 A1 | 5/2010 | Froman et al. | |
| 2010/0136679 A1 * | 6/2010 | Min | B01L 3/5021 435/325 |
| 2010/0140182 A1 * | 6/2010 | Chapman | A61M 1/029 210/741 |
| 2010/0155319 A1 | 6/2010 | Felix et al. | |
| 2010/0317106 A1 | 12/2010 | Levine et al. | |
| 2011/0033925 A1 | 2/2011 | Duffy et al. | |
| 2011/0251041 A1 * | 10/2011 | Chavarria | A61M 1/3693 494/4 |
| 2012/0225766 A1 | 9/2012 | Seubert et al. | |
| 2013/0072402 A1 | 3/2013 | Takamura et al. | |
| 2014/0087360 A1 | 3/2014 | Woodside | |
| 2014/0161688 A1 | 6/2014 | Campton et al. | |
| 2014/0349828 A1 | 11/2014 | U'ren et al. | |
| 2015/0231631 A1 | 8/2015 | Campton et al. | |
| 2017/0074759 A1 | 3/2017 | Campton et al. | |
| 2017/0191911 A1 | 7/2017 | Campton et al. | |

\* cited by examiner

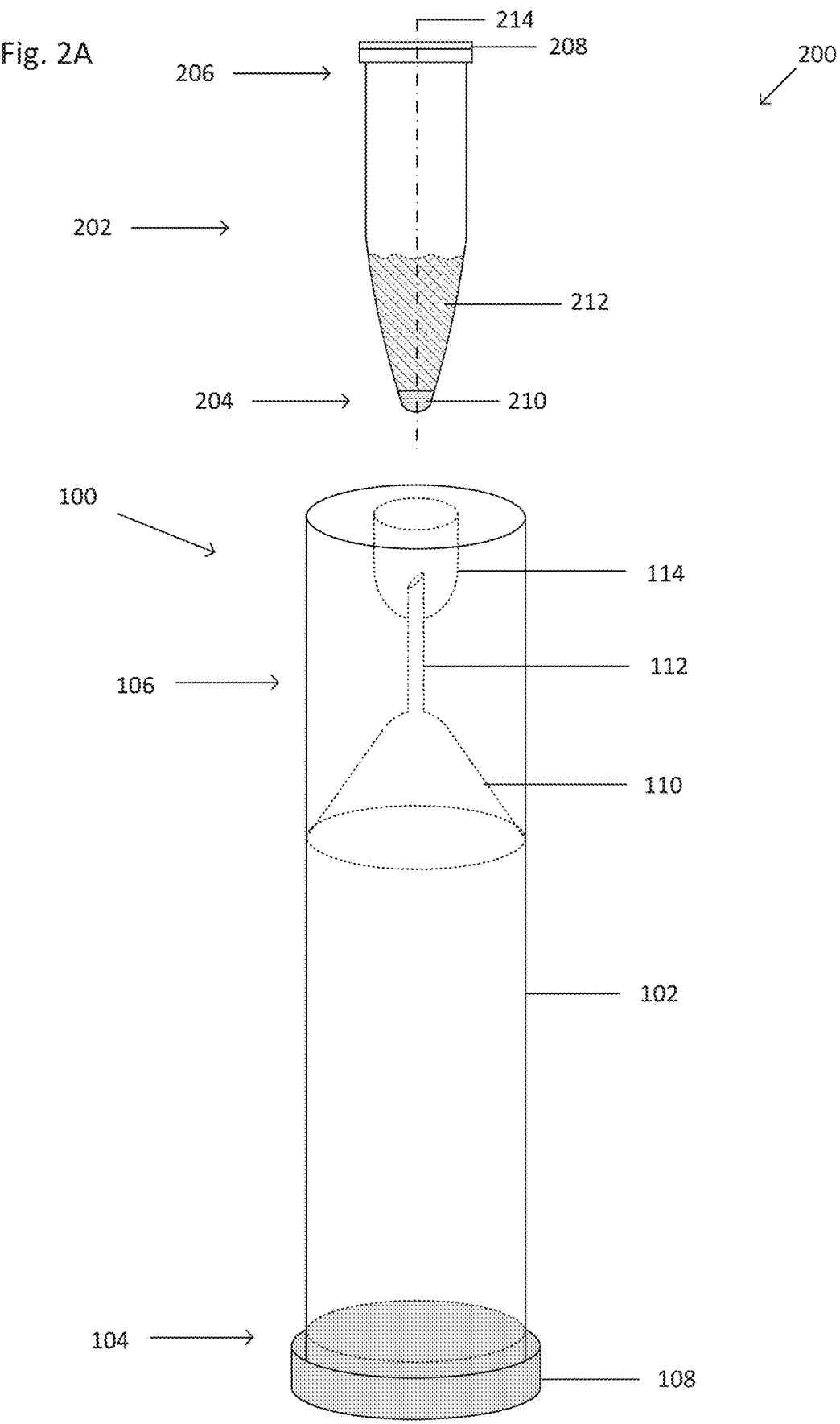

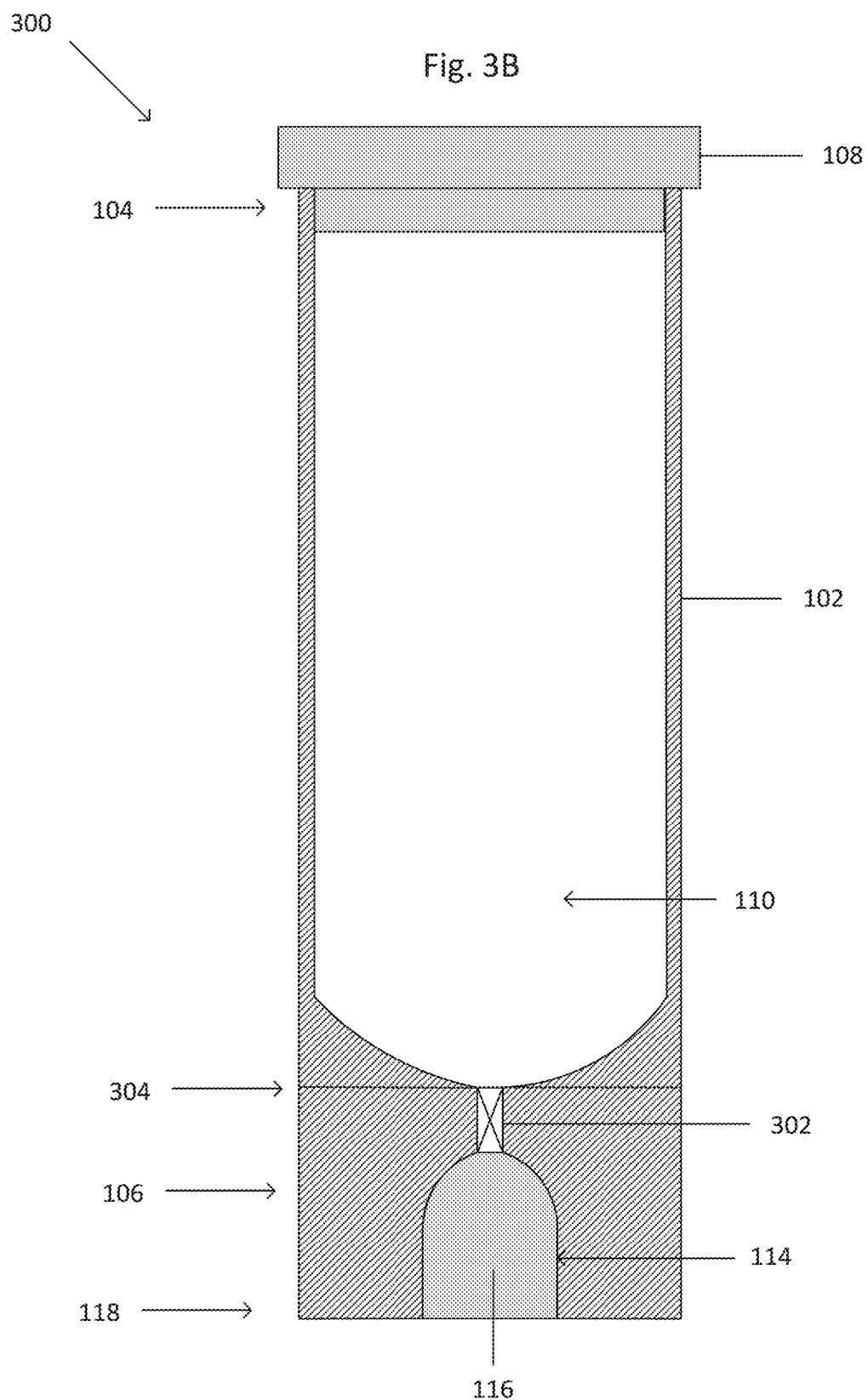

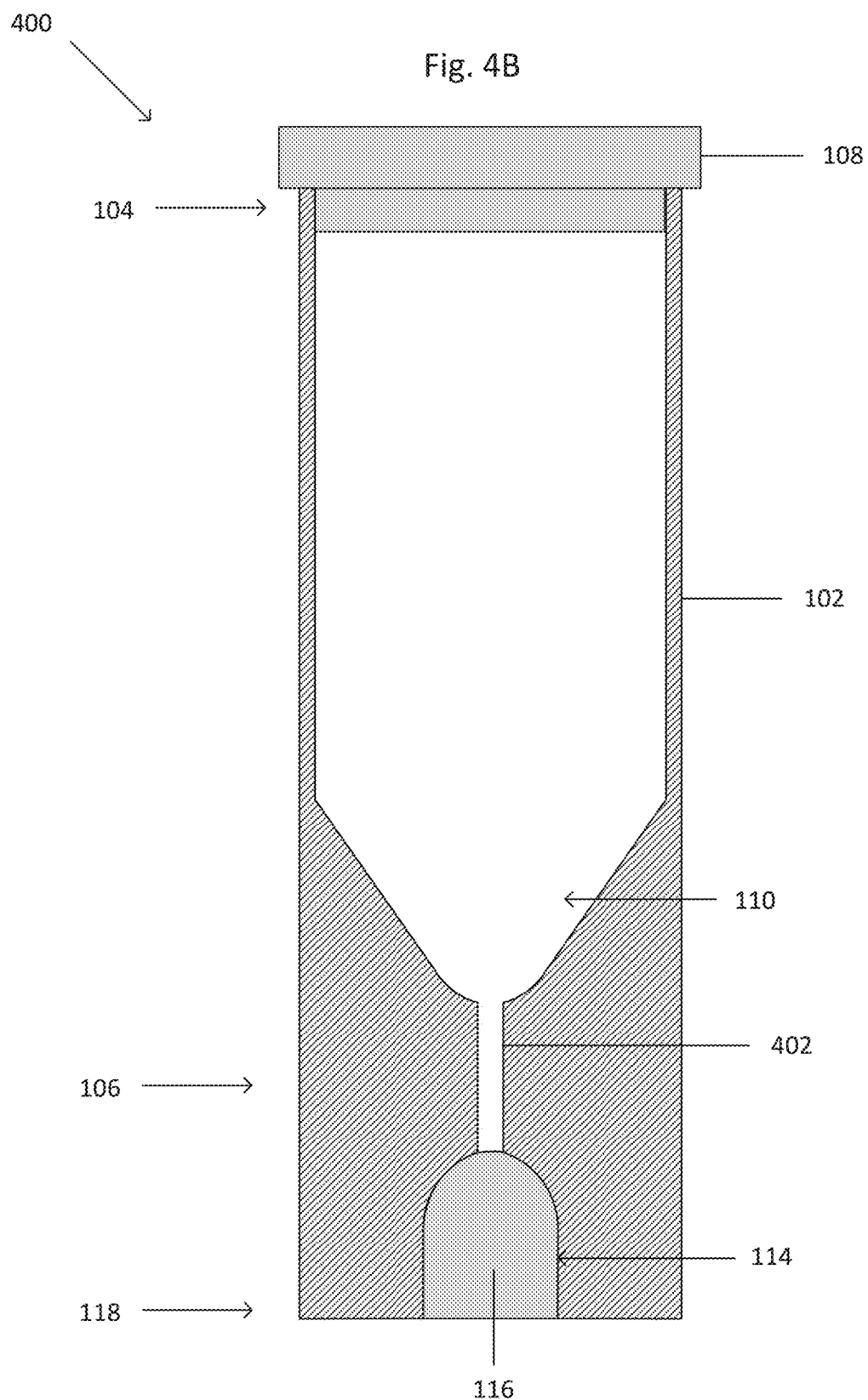

Fig. 7E
Fig. 7F
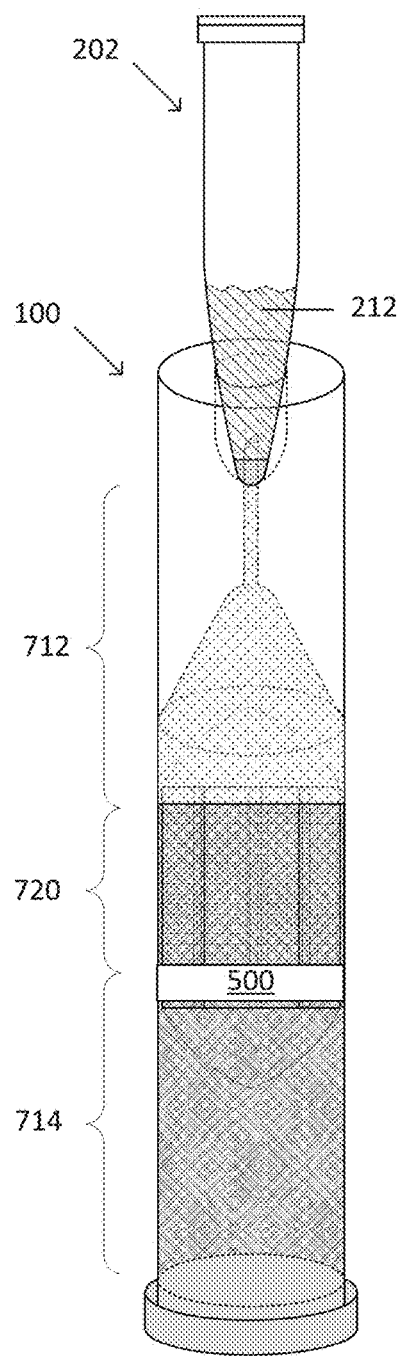
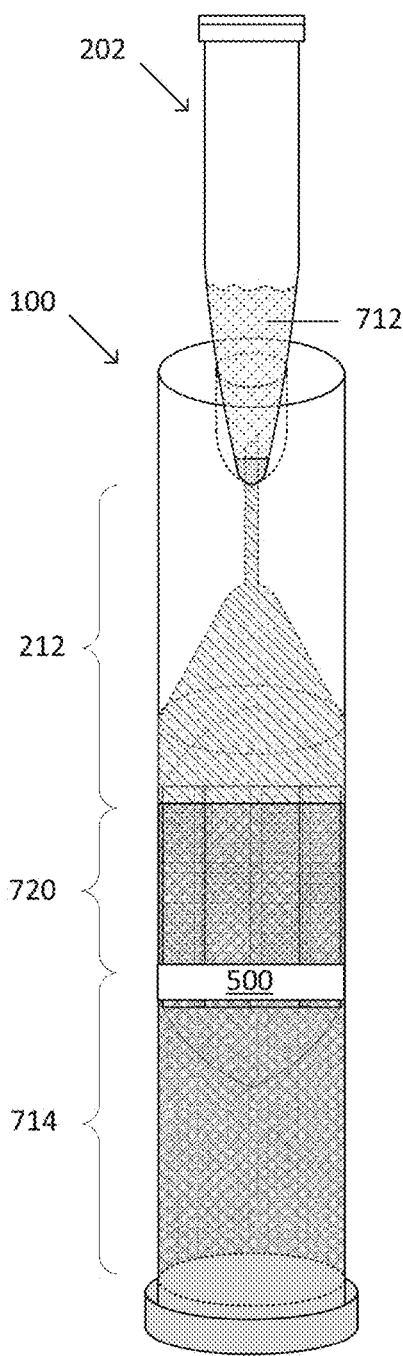

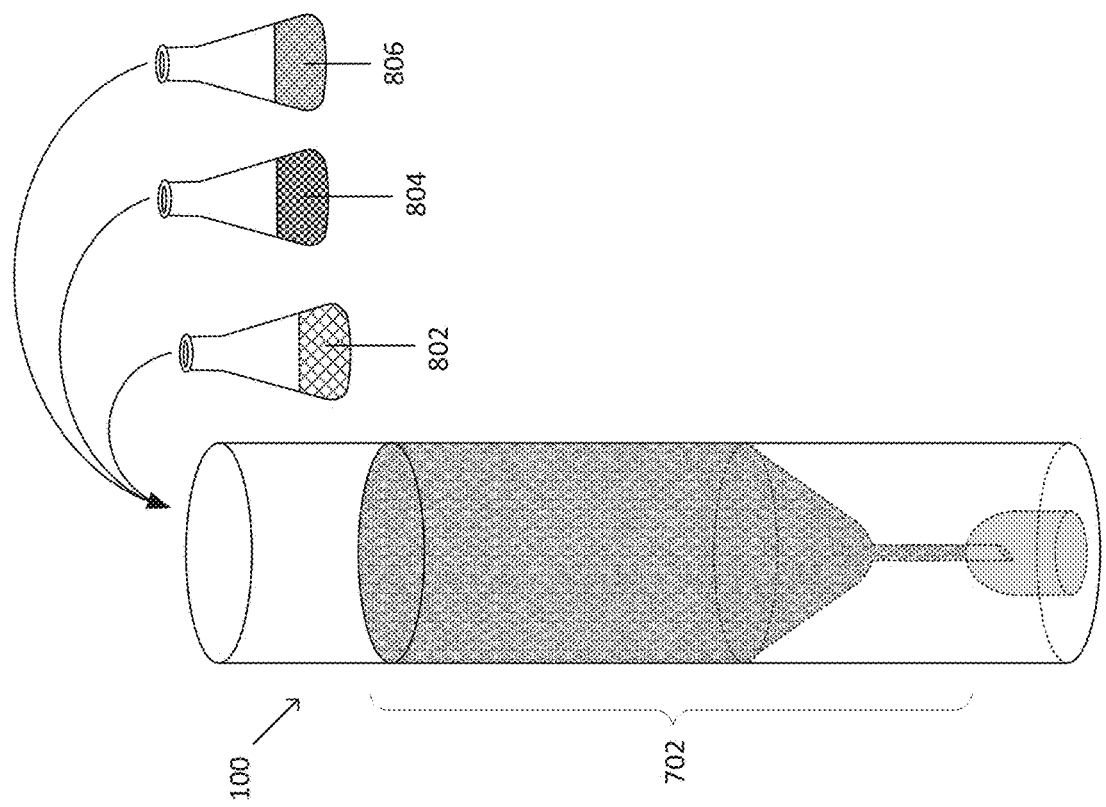
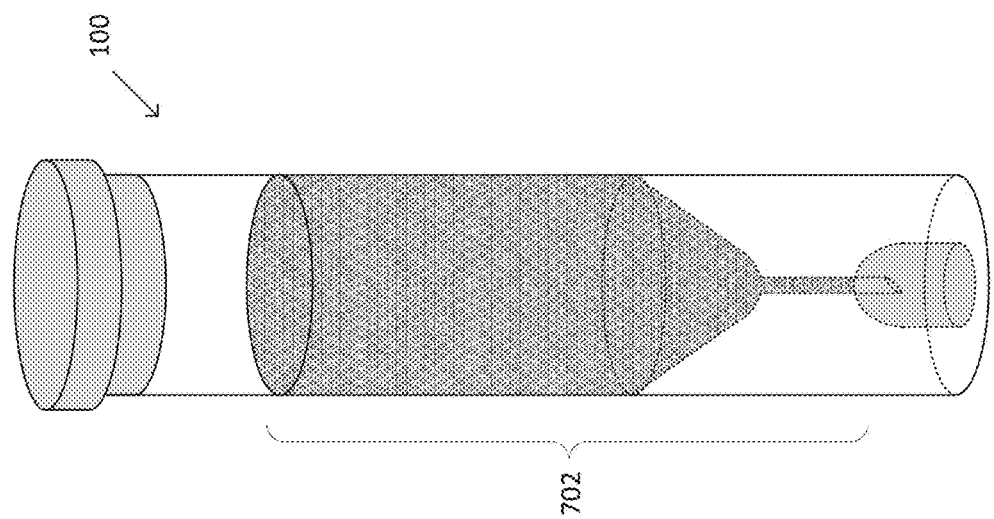
Fig. 8B
Fig. 8A

Fig. 8D
Fig. 8E
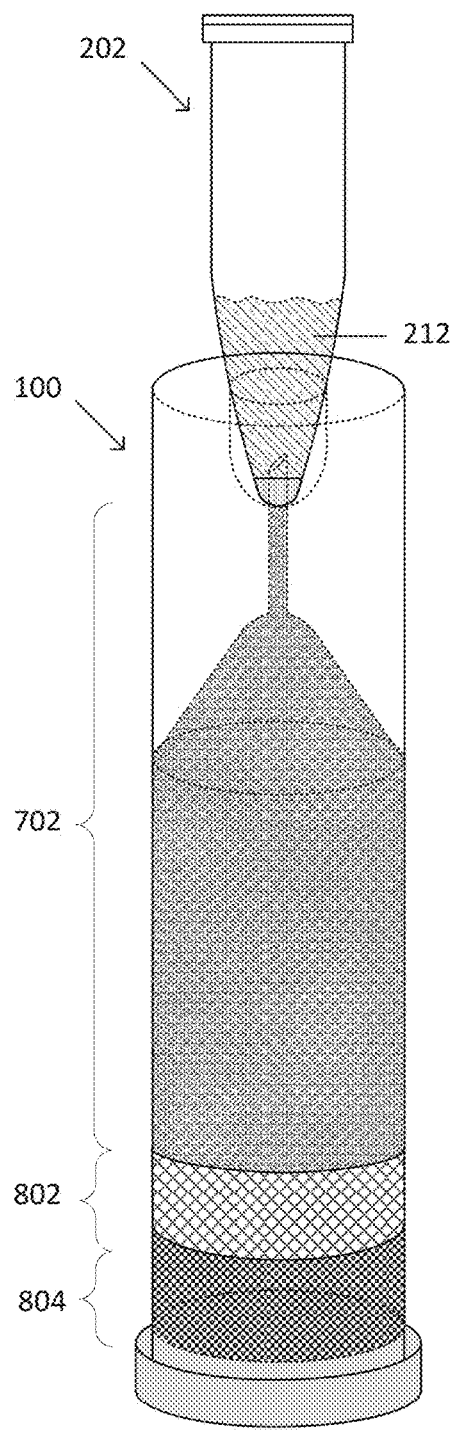
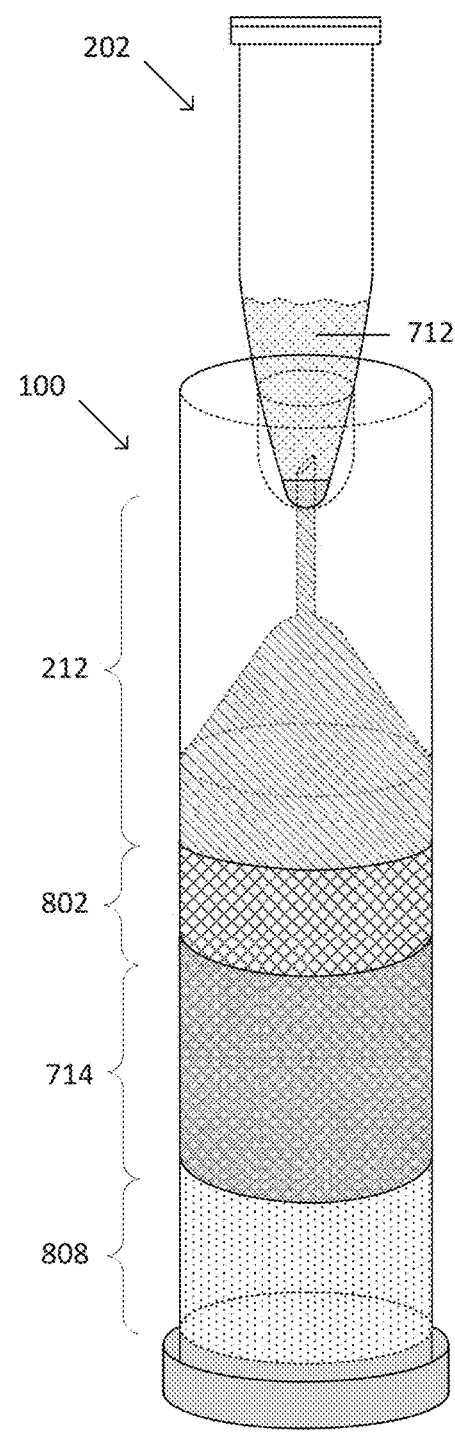

APPARATUS, SYSTEM, AND METHOD FOR COLLECTING A TARGET MATERIAL

CROSS REFERENCE TO RELATED APPLICATIONS

This application is a continuation of application Ser. No. 15/264,257, filed Sep. 13, 2016, which claims the benefit of Provisional Application No. 62/345,172, filed Jun. 3, 2016, and which is also a continuation-in-part of application Ser. No. 14/610,522, filed Jan. 30, 2015 (now U.S. Pat. No. 9,539,570, issued Jan. 10, 2017), which claims the benefit of Provisional Application No. 61/935,457, filed Feb. 4, 2014, and is also a continuation-in-part of application Ser. No. 14/495,449, filed Sep. 24, 2014 (now U.S. Pat. No. 9,039,999, issued May 26, 2016), which is a continuation-in-part of application Ser. No. 14/090,337, filed Nov. 26, 2013, now abandoned, which claims the benefit of Provisional Application No. 61/732,029, filed Nov. 30, 2012; Provisional Application No. 61/745,094, filed Dec. 21, 2012; Provisional Application No. 61/791,883, filed Mar. 15, 2013; Provisional Application No. 61/818,301, filed May 1, 2013; and Provisional Application No. 61/869,866, filed Aug. 26, 2013; and is also a continuation-in-part of application Ser. No. 14/266,939, filed May 1, 2014, now abandoned, which claims the benefit of Provisional Application No. 61/818,301, filed May 1, 2013, Provisional Application No. 61/869,866, filed Aug. 26, 2013, and Provisional Application No. 61/935,457, filed Feb. 4, 2014.

TECHNICAL FIELD

This disclosure relates generally to density-based fluid separation and, in particular, to retrieving target material from a suspension.

BACKGROUND

Suspensions often include materials of interests that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as ova, fetal cells, endothelial cells, parasites, bacteria, and inflammatory cells, and viruses, including HIV, cytomegalovirus, hepatitis C virus, and Epstein-Barr virus. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field or fluorescence microscopy.

On the other hand, materials of interest that occur in a suspension with very low concentrations are especially difficult if not impossible to detect and analyze using many existing techniques. As a result, practitioners, researchers, and those working with suspensions continue to seek systems and methods for accurate analysis of suspensions for the presence or absence rare materials of interest.

DESCRIPTION OF THE DRAWINGS

FIGS. 2A-2C show an example tube-processing vessel system.
FIGS. 3A-3B show an example tube.
FIGS. 4A-4B show an example tube.
FIGS. 7A-7F show an example system retrieving target material.
FIGS. 8A-8E show an example system retrieving target material.

DETAILED DESCRIPTION

This disclosure is directed to an apparatus, system and method for retrieving target material from a suspension. A system includes a processing vessel, a displacement fluid, and a tube. The tube includes a funnel, a cannula, and a cavity. The cannula allows for fluid communication between the funnel and the cavity, such that the processing vessel is inserted into the cavity, and the cannula extends into the processing vessel.

Figure 1A:
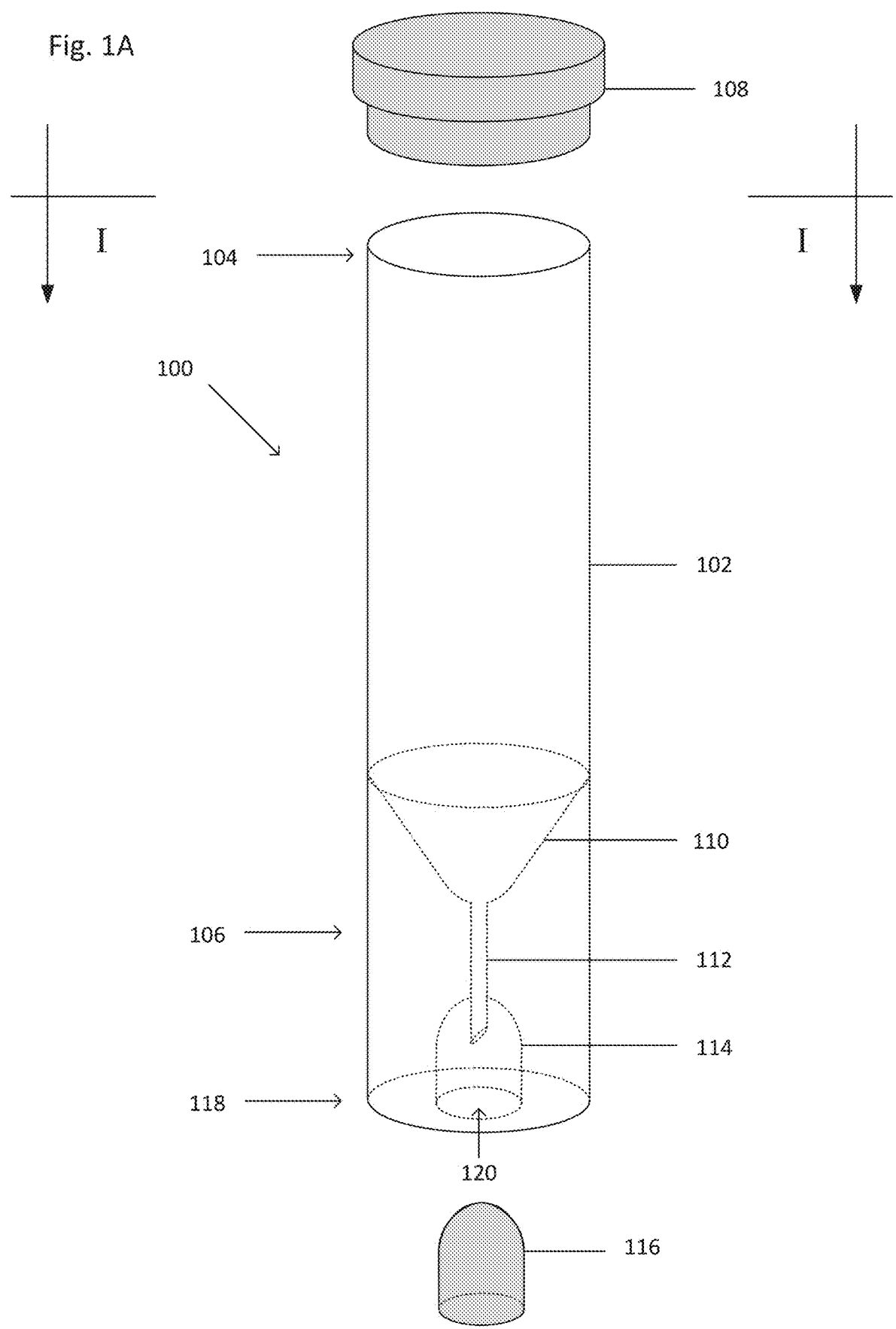
FIGS. 1A-1B show an example tube.
Figure 1B:
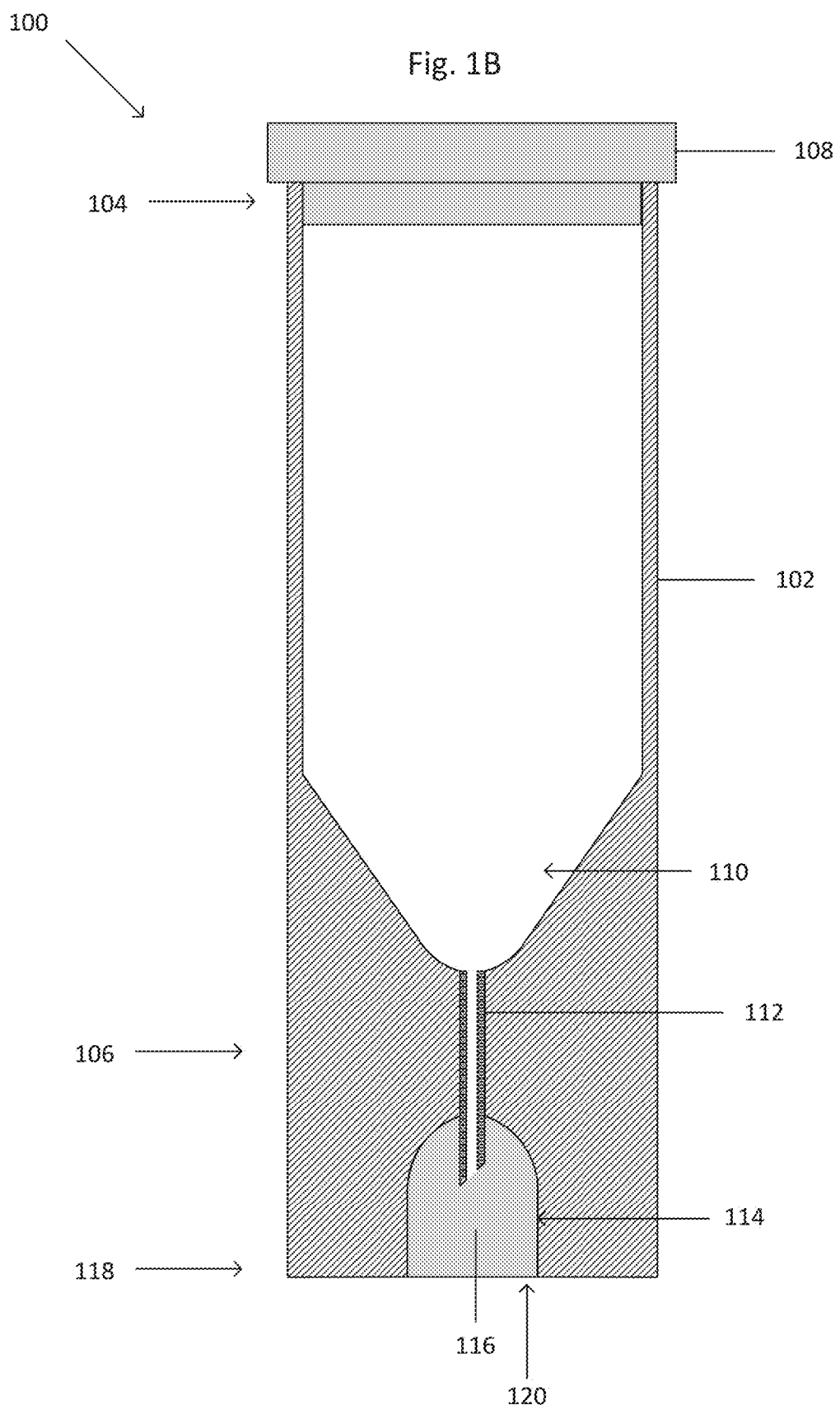

FIG. 1A shows an isometric view of a tube 100. FIG. 1B shows a cross-sectional view of the tube 100 taken along the line I-I shown in FIG. 1A. The tube 100 may be any appropriate size or cross-sectional shape (e.g. cylindrical, elliptical, triangular, square, rectangular, or the like. The tube 100 includes a main body 102 having a sidewall which connects a first end 104, a second end 118, and a collection segment 106 between the first end 104 and the second end 118. The tube 100 may also include a cap 108 to seal or close the first end 104, which may be open. The collection segment 106 includes a funnel 110, a cannula 112, and a cavity 114.

The funnel 110 tapers away from the first end 104 towards the second end 118. The funnel 110 channels target material from a mouth of the funnel 110 into the cannula 112 which is connected to, and in fluid communication with, an apex of the funnel 110. The apex of the funnel 110 has a smaller diameter than the mouth of the funnel 110. The funnel 110 is formed by a tapered wall that may be straight, curvilinear, arcuate, or the like. The funnel 110 may be any appropriate shape, including, but not limited to, tubular, hemispherical, parabolic, conical, rectangular, pyramidal, or the like.

The cannula 112, such as a tube or a needle, including, but not limited to a non-coring needle, extends from the apex of the concave opening 114 and into the cavity 114. The cavity 114 is a concave opening extending from an aperture 120 in the second end 118 towards the first end 104. The cavity 114 may accept and support a processing vessel (not shown). The cavity 114 may be any appropriate depth to accept and support the processing vessel (not shown). The cavity 114 may be threaded to engage a threaded portion of the processing vessel (not shown). The cannula 112 may extend any appropriate distance into the cavity 114 in order to extend into, to puncture the base of, or be inserted into, the processing vessel (not shown). The cannula 112 may include a flat tip, a beveled tip, a sharpened tip, or a tapered tip. Furthermore, the cavity 114 may be any appropriate shape, including, but not limited to, tubular, hemispherical, parabolic, conical, rectangular, pyramidal, or the like. The cannula 112 can be composed of a variety of different materials including, but not limited to, a ceramic; metals; organic or inorganic materials; and plastic materials, such as a polypropylene, acrylic, polycarbonate, or the like; and combinations thereof. The cannula 112 may have a tip along a longitudinal axis of the cannula.

The first end 104 is sized to receive a cap 108. The cap 108 may be composed of re-sealable rubber or other suitable re-sealable material that can be repeatedly punctured with a needle or other sharp implement to access the contents stored in the tube 100 interior and re-seals when the needle or implement is removed. Alternatively, the cap 108 may be a screw cap with threads to engage complementary threads within or around the first end 104. Alternatively, a clip may be placed over the cap 108 and the first end 104 of the tube 100 to increase the pressure exerted by the cap 108 on the first end 104 to provide a more secure fit. The clip may be a two-piece ring, a one piece ring wrapping around the full circumference of the tube 100, or a one piece ring wrapping around less than the full circumference of the tube 100, such as one-half (½), five-eighths (⅝), two-thirds (⅔), three-quarters (¾), seven-eighths (⅞), or the like. Alternatively, the cap 108 may be temporarily or permanently affixed to the main body 102 of the tube 100 via the first end 104, such as by welding (e.g. ultrasonic welding), adherence (e.g. an adhesive), clamping (e.g. a sealing ring, crimper, clamp, or the like), or any other appropriate manner for temporarily or permanently affixing two pieces.

The tube 100 may also include a plug 116 to be inserted into the cavity 114 to inhibit fluid from escaping from the cannula 112 when the cannula 112 is pointed downward. The plug 116 may be composed of re-sealable rubber or other suitable re-sealable material that can be repeatedly punctured with the cannula 112 and re-seals when the cannula 112 is removed. Alternatively, the plug 116 may be a screw cap with threads to engage complementary threads within the cavity 114 or outside or on the second end 118. Alternatively, a clip may be placed over the plug 116 and the first end 104 of the tube 100 to increase the pressure exerted by the plug 116 on the first end 104 to provide a more secure fit. The clip may be a two-piece ring, a one piece ring wrapping around the full circumference of the tube 100, or a one piece ring wrapping around less than the full circumference of the tube 100, such as one-half (½), five-eighths (⅝), two-thirds (⅔), three-quarters (¾), seven-eighths (⅞), or the like.

The tube 100 can be composed of a variety of different materials including, but not limited to, a ceramic; metals; organic or inorganic materials; and plastic materials, such as polyoxymethylene ("Delrin®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides ("aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrile butadiene-styrene copolymer, butyl rubber, ethylene propylene diene monomer; and combinations thereof. The tube 100 may be rigid or flexible.

Figure 2B:
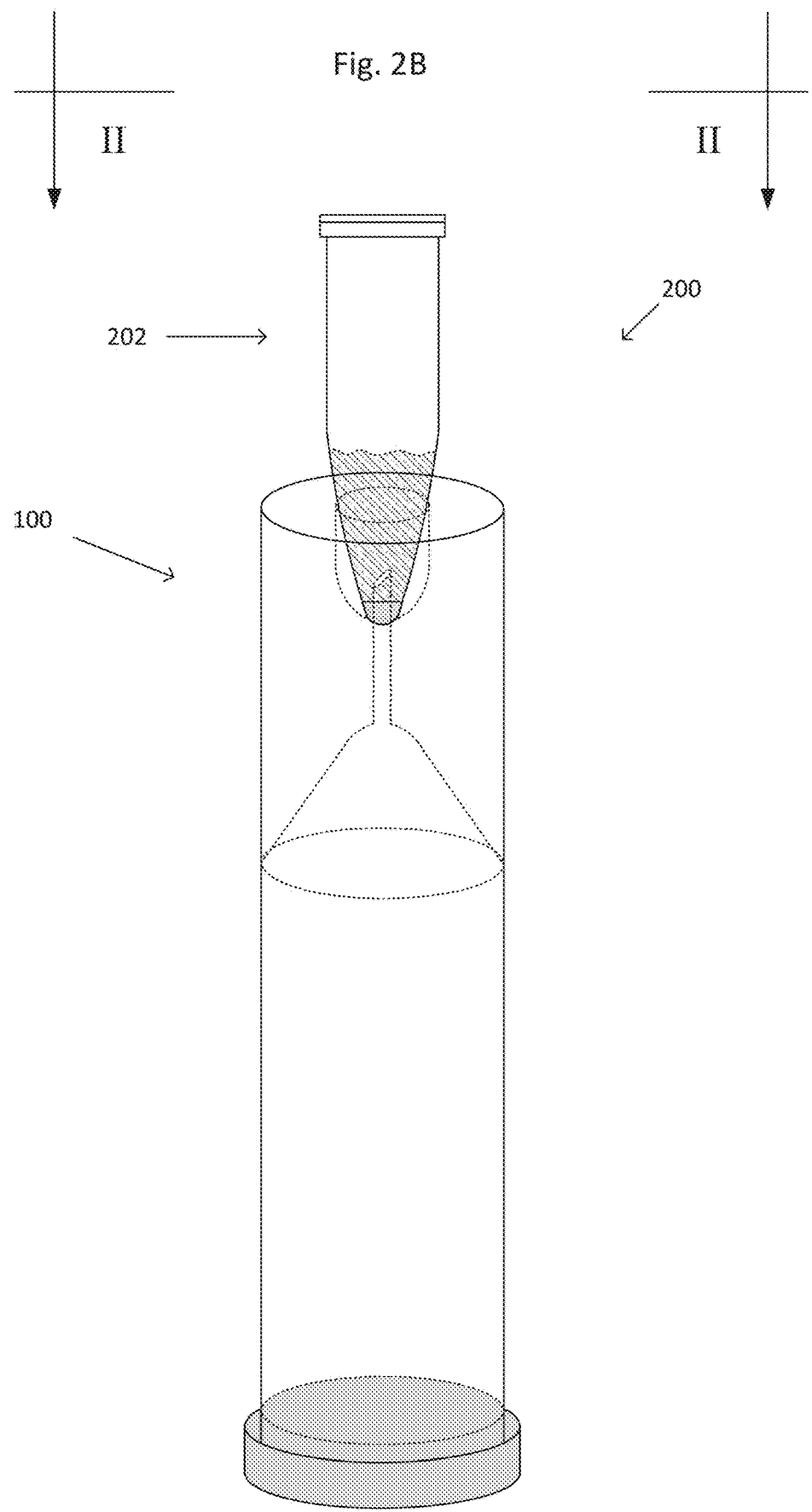
Figure 2C:
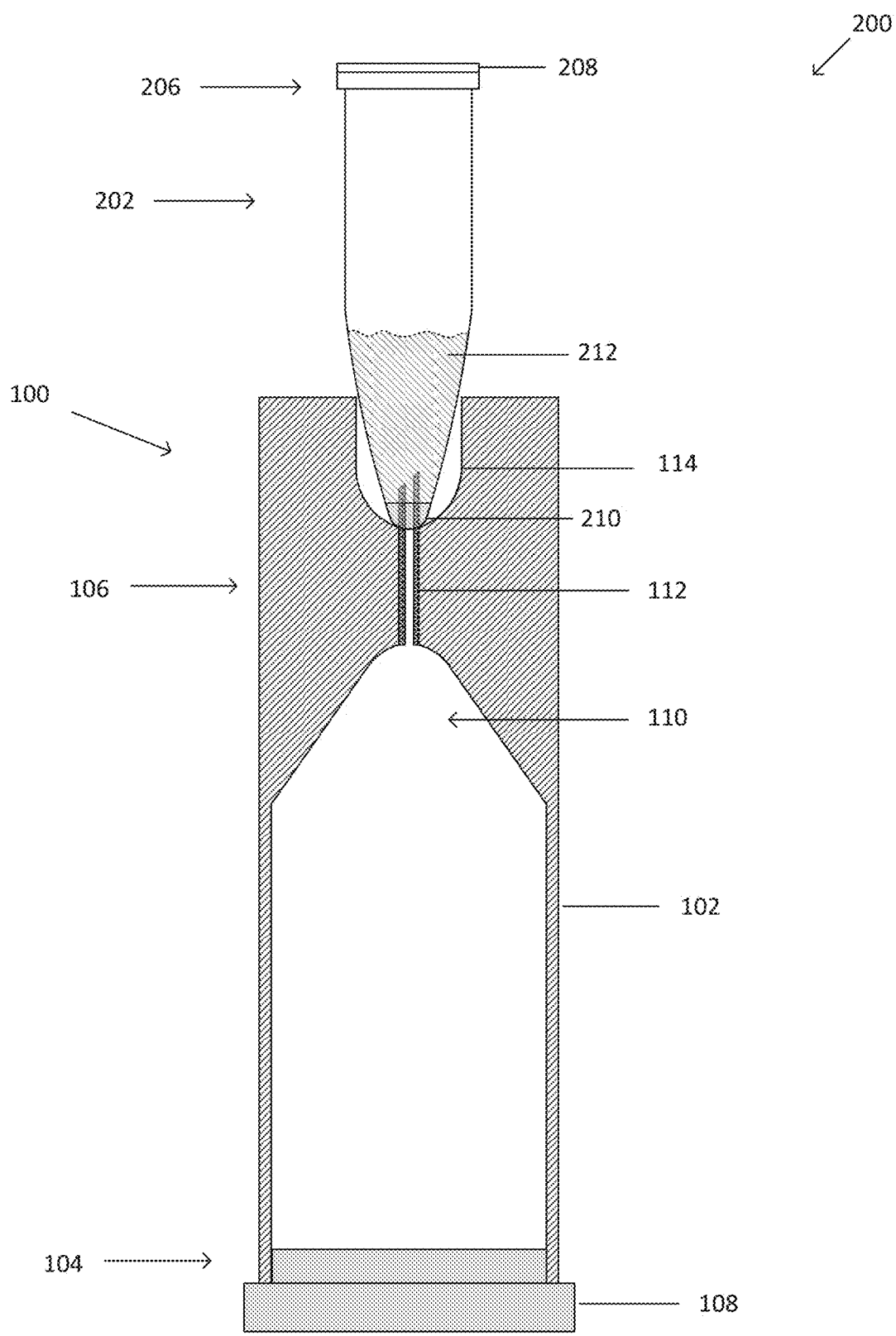

FIG. 2A shows an exploded view of the example tube 100 and processing vessel 202. FIG. 2B shows an isometric view of the processing vessel 202 inserted into the cavity 114 at the collection segment 106 of the tube 100 to form a tube-processing vessel system 200. FIG. 2C shows a cross-sectional view of the processing vessel 202 inserted into the cavity 114 at the collection segment 106 of the tube 100 taken along the line II-II shown in FIG. 2B. The tube 100 and processing vessel 202 form a tube-processing vessel system 200. The processing vessel 202 may be an eppendorf tube, a syringe, or a test tube, and has a closed end 204 and an open end 206. The open end 206 is sized to receive a cap 208. The cap 208 may be composed of re-sealable rubber or other suitable re-sealable material that can be repeatedly punctured with a needle or other sharp implement to access the contents stored in the processing vessel 202 interior and re-seals when the needle or implement is removed. Alternatively, the processing vessel 202 may also have two open ends that are sized to receive caps. The processing vessel 202 may have a tapered geometry that widens or narrows toward the open end 206; the processing vessel 202 may have a generally cylindrical geometry; or, the processing vessel 202 may have a generally cylindrical geometry in a first segment and a cone-shaped geometry in a second segment, where the first and second segments are connected and continuous with each other. Although at least one segment of the processing vessel 202 has a circular cross-section, in other embodiments, the at least one segment can have elliptical, square, triangular, rectangular, octagonal, or any other suitable cross-sectional shape. The processing vessel 202 can be composed of a transparent, semitransparent, opaque, or translucent material, such as plastic or another suitable material. The processing vessel includes a central axis 214, which when inserted into the cavity 114 is coaxial with a central axis of the tube 100. The processing vessel 202 may also include a plug 210 at the closed end 204 to permit the introduction of the target material or to exchange the target material with a displacement fluid 212. The closed end 204 may be threaded to provide for a threaded connection with a threaded cavity (not shown) of the tube 100. The processing vessel 202 may be composed of glass, plastic, or other suitable material.

The plug 210 may be composed of re-sealable rubber or other suitable re-sealable material that can be repeatedly punctured with a needle or other sharp implement to access the contents of the processing vessel 202 interior or permit introduction of contents into the processing vessel 202 and re-seals when the needle or implement is removed. The plug 210 may be inserted into the processing vessel 202 such that a seal is maintained between the plug 210 and the processing vessel 202, such as by an interference fit. Alternatively, the plug 210 can be formed in the closed end 204 of the processing vessel 202 using heated liquid rubber that can be shaped while warm or hot and hardens as the rubber cools. An adhesive may be used to attach a plug 210 to the inner wall of the processing vessel can be a polymer-based adhesive, an epoxy, a contact adhesive or any other suitable material for bonding or creating a thermal bond. Alternatively, the plug 210 may be injected into the processing vessel 202. Alternatively, the plug 210 may be thermally bonded to the processing vessel 202.

The cannula 112, for example, may have a tapered tip that punctures the plug 210 and extends into an inner cavity of the processing vessel 202 with the shaft of the cannula 112 not extending into the inner cavity of the processing vessel 202. As explained in greater detail below, the inner cavity of the processing vessel 202 holds the target material. The cannula 112 may be covered by a resealable sleeve (not shown) to prevent the target material from flowing out unless the processing vessel 202 is in the cavity 114 to a depth that allows the cannula 112 to just penetrate the processing vessel 202. The resealable sleeve (not shown) covers the cannula 112, is spring-resilient, can be penetrated by the cannula 112, and is made of an elastomeric material capable of withstanding repeated punctures while still maintaining a seal.

The processing vessel 202 may be loaded with a displacement fluid 212 prior to insertion into the tube 100. The displacement fluid 212 displaces the target material, such that when the processing vessel 202 is inserted into the primary vessel tube 100, which includes the target material, and the tube 100 and the processing vessel 202 undergo centrifugation, the displacement fluid 212 flows out of the processing vessel 202 and into the tube 100, and, through displacement, such as through buoyant displacement (i.e. lifting a material upwards), pushes the target material through the cannula 112 and into the processing vessel 202.

The displacement fluid 212 has a greater density than the density of the desired target material of the suspension (the density may be greater than the density of a subset of suspension fractions or all of the suspension fractions) and is inert with respect to the suspension materials. For example, the displacement fluid may have a density that is approximately 0.001 to approximately 0.005 g/cm$^3$ greater than the density of the desired target material. The displacement fluid 212 may be miscible or immiscible in the suspension fluid. Examples of suitable displacement fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

The processing vessel 202 may also include a processing solution (not shown) to effect a transformation on the target material when the target material enters the processing vessel 202. The processing solution (not shown) may be a preservative, a cell adhesion solution, a dye, or the like. Unlike the displacement fluid 212, most, if not all, of the processing solution (not shown) remains within the processing vessel 202 upon centrifugation, thereby effecting the transformation on the target material in one manner or another (i.e. preserving, increasing adhesion properties, or the like). The processing solution (not shown) may be introduced as a liquid or as a liquid contained in a casing. The casing may be dissolvable in an aqueous solution but not in the displacement fluid 212 (such as gel cap); or, the casing may be breakable, such that the casing breaks when the processing vessel 202 is shaken in a vortex mixer. Additionally, more than one processing solution may be used.

The processing vessel 202 may include a flexible cap that can be pushed to dispense a pre-determined volume therefrom and onto a substrate, such as a slide or a well plate. The cap 208 may be flexible or the cap 208 may be removed and the flexible cap inserted into the open end 206. Alternatively, the processing vessel 202 may be attached to (i.e. after accumulating the target material) or may include a dispenser, which is capable of dispensing a pre-determined volume of target material from the processing vessel 202 onto another substrate, such as a microscope slide. The dispenser may repeatedly puncture the re-sealable cap 208 or compress the material within the processing vessel 202 to withdraw and dispense the pre-determined volume of target material onto the substrate. Alternatively, the cap 208 may be removed and the dispenser (not shown) may be inserted directly into the processing vessel 202 to dispense the buffy coat-processing solution mixture.

Figure 3A:
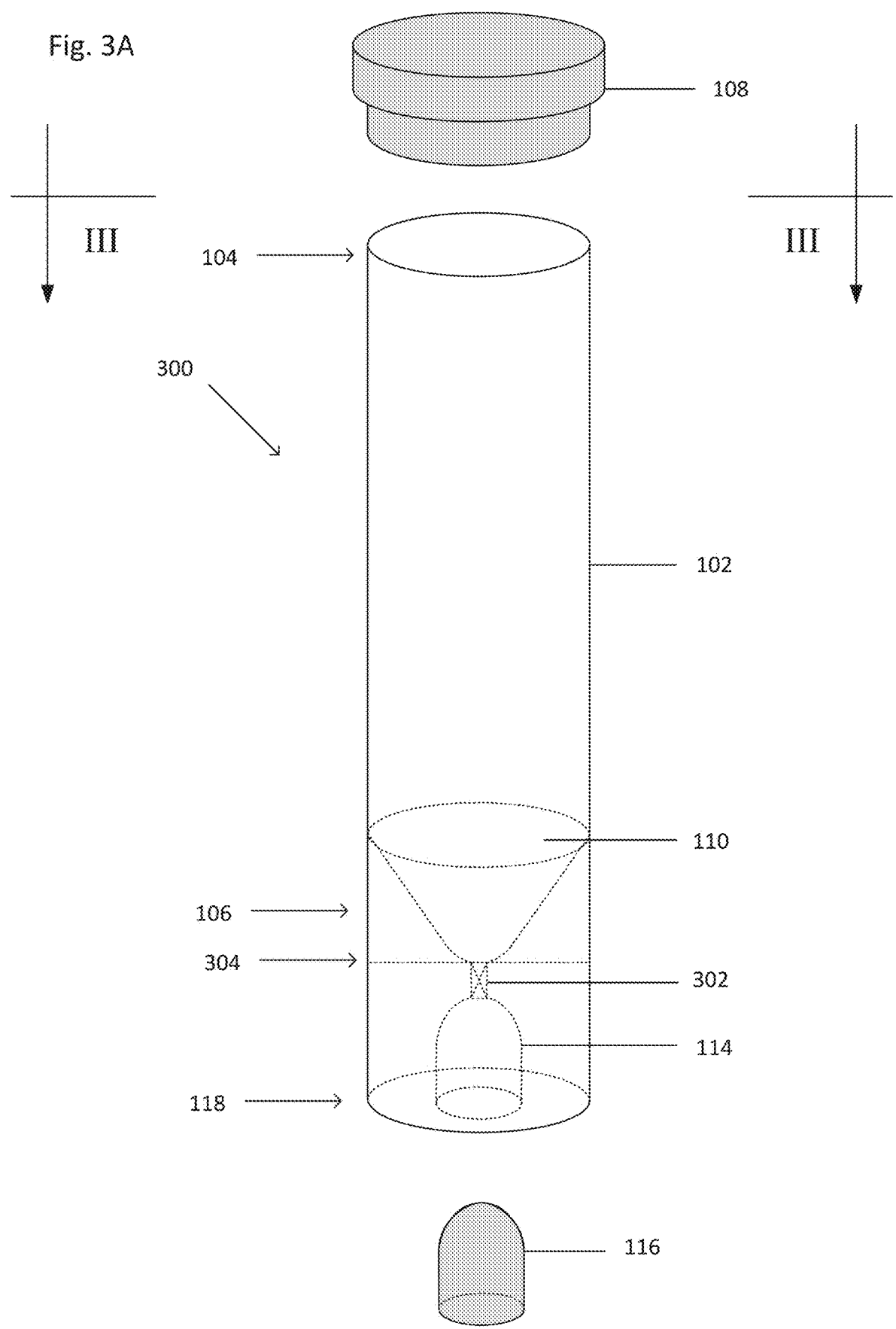

FIG. 3A shows an isometric view of a tube 300. FIG. 3B shows a cross-sectional view of the tube 300 taken alone the line III-III. The tube 300 is similar to the tube 100 except that the tube 300 includes a valve 302 instead of a cannula 112 to provide a passageway between the funnel 110 and the cavity 114. When undergoing centrifugation, the valve 302 opens to permit fluid flow between the funnel 110 and the cavity 114. When not undergoing centrifugation, the valve 302 is closed to inhibit fluid flow between the funnel 110 and the cavity 114. The valve 302 may include but is not limited to a ball check valve, a diaphragm check valve, a swing check valve, a tilting disk check valve, a lift check valve, and a duckbill valve. Alternatively, the valve 302 is closed when the centrifugal forces are less than or equal to a predetermined amount and the valve 320 is open when the centrifugal forces are greater than or equal to a predetermined amount. The predetermined amount may include, but is not limited to, 2 g, 5 g, 10 g, 100 g, 1000 g, 2000 g, 2500 g, 3000 g, 5000 g, or 10000 g, where g is the force of gravity.

The collection end 106 may include a break-point 304 where to permit the cavity 114 and the valve 302 to be separated from the funnel 110 so that the target material may be removed and retained in a single vessel for subsequent processing. The break-point 304 may include threads, a tongue and groove joint, a dovetail joint, or any appropriate connection method.

Before centrifugation and after inverting the tube 300, the plug 116 may be removed from the cavity 114 and the cavity 114 may be loaded with the displacement fluid 212. The displacement fluid 212 displaces the target material, such that when the tube 300 undergoes centrifugation, the displacement fluid 212 flows out of the processing cavity 114 and into the funnel 110 via the open valve 302, and, through displacement, such as through buoyant displacement (i.e. lifting a material upwards), pushes the target material through the open valve 302 and into the cavity 114. During centrifugation, the cavity 114 may be sealed by a cover (not shown) which may include threads, may be puncturable and resealable, or may be a one-time use, such as a foil.

Figure 4A:
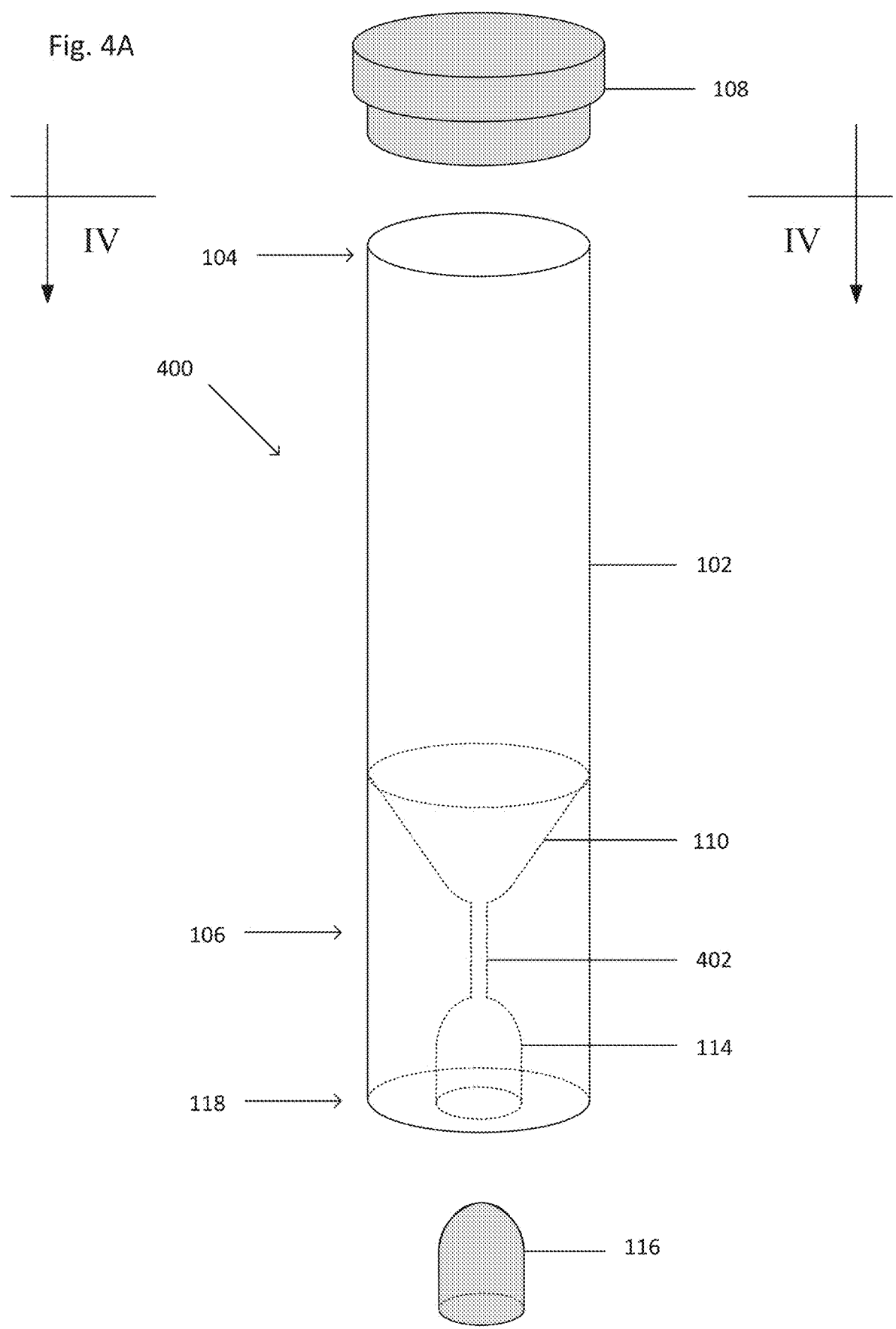

FIG. 4A shows an isometric view of a tube 400. FIG. 4B shows a cross-sectional view of the tube 400 taken alone the line IV-IV. The tube 400 is similar to the tube 100 except that the tube 400 includes a hole 402 instead of a cannula 112 to provide a passageway between the funnel 110 and the cavity 114. The hole 402 has a diameter that is sized to inhibit fluid communication between the funnel 110 and the cavity 114 before and after centrifugation and to allow fluid communication between the funnel 110 and the cavity 114 during centrifugation. The diameter, for example, may be based on the respective surface tensions of the displacement fluid 212 and the target material.

Before centrifugation and after inverting the tube 400, the plug 116 may be removed from the cavity 114 and the cavity 114 may be loaded with the displacement fluid 212. The displacement fluid 212 displaces the target material, such that when the tube 400 undergoes centrifugation, the displacement fluid 212 flows out of the processing cavity 114 and into the funnel 110 via the hole 402, and, through displacement, such as through buoyant displacement (i.e. lifting a material upwards), pushes the target material through the 402 and into the cavity 114. During centrifugation, the cavity 114 may be sealed by a cover (not shown) which may include threads, may be puncturable and resealable, or may be a one-time use, such as a foil.

Sealing Ring

Figure 5A:
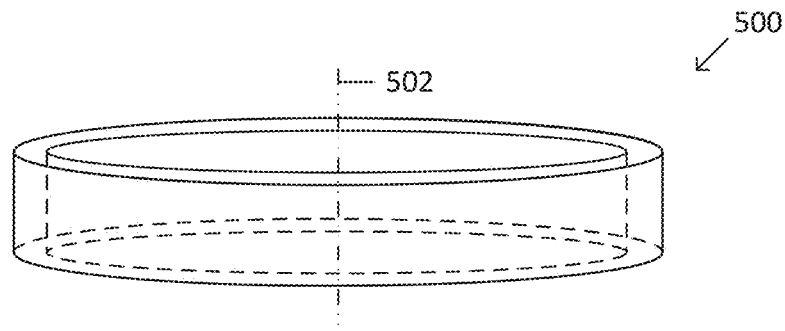
FIGS. 5A-5G show example sealing rings.
Figure 5B:
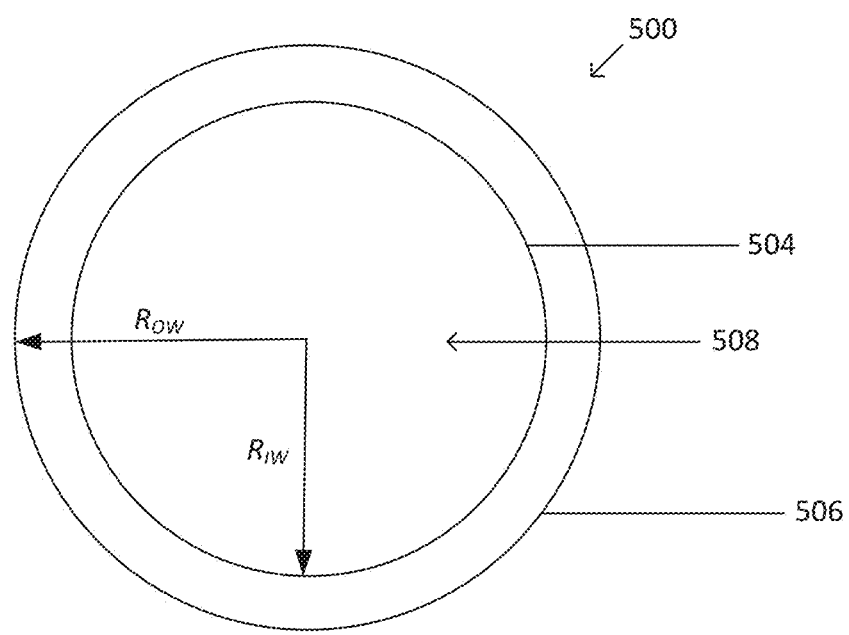

FIG. 5A shows an isometric view of a sealing ring 500. FIG. 5B shows a top down view of the sealing ring 500. Dot-dashed line 502 represents the central or highest-symmetry axis of the sealing ring 500. The sealing ring 500 includes an inner wall 504, an outer wall 506, and a cavity 508. In FIG. 5B, $R_{IW}$ represents the radial distance from the center of the sealing ring 500 to the inner wall 504, and $R_{OW}$ represents the radial distance from the center of the sealing ring 500 to the outer wall 506. The sealing ring 500 is configured to fit around a primary vessel, such as a tube. The cavity 508 is sized and shaped to receive the primary vessel. The sealing ring 500 may be tightened, such that the size of the cavity 508 and the radii of the inner and outer walls 504 and 506 are reduced by circumferentially applying an approximately uniform, radial force, such as the radial force created by a clamp, around the outer wall 506 directed to the central axis 502 of the sealing ring 500. When the sealing ring 500 is tightened around the primary vessel, the uniform force applied to the sealing ring 500 is applied to the primary vessel, thereby causing the primary vessel to constrict. When the radial force is removed from the sealing ring 500, the sealing ring 500 remains tightened and in tension around the primary vessel.

Figure 5C:
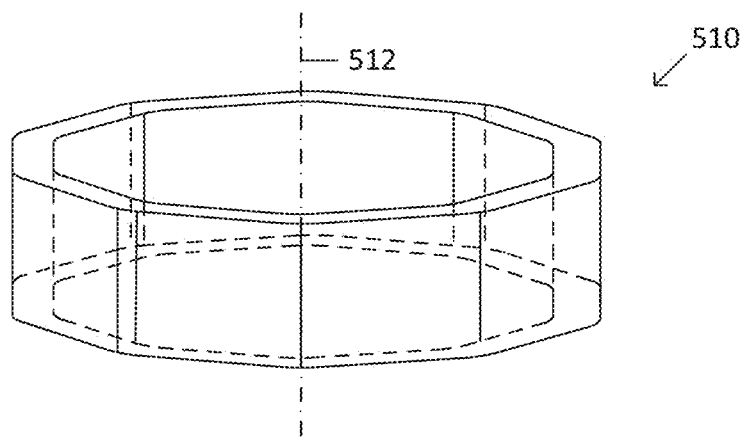
Figure 5D:
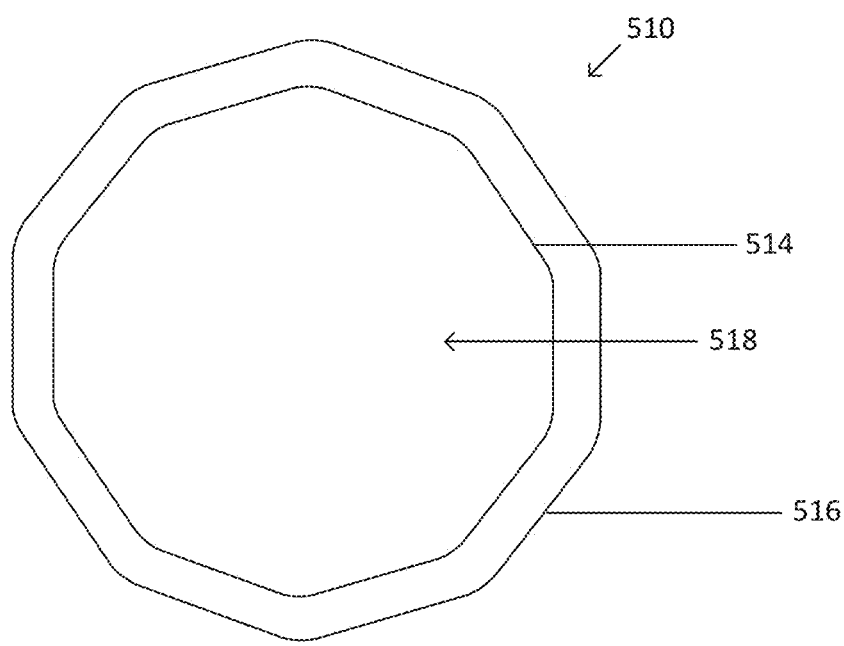

The sealing ring may be any shape, including, but not limited to, circular, triangular, or polyhedral. FIG. 5C shows an isometric view of a sealing ring 510. FIG. 5D shows a top down view of the sealing ring 510. Sealing ring 510 is similar to sealing ring 500, except sealing ring 510 is polyhedral. Dot-dashed line 512 represents the central or highest-symmetry axis of the sealing ring 510. The sealing ring 510 includes an inner wall 514, an outer wall 516, and a cavity 518. The sealing ring may be composed of a metal, such as brass, a polymer, or combinations thereof.

Figure 5E:
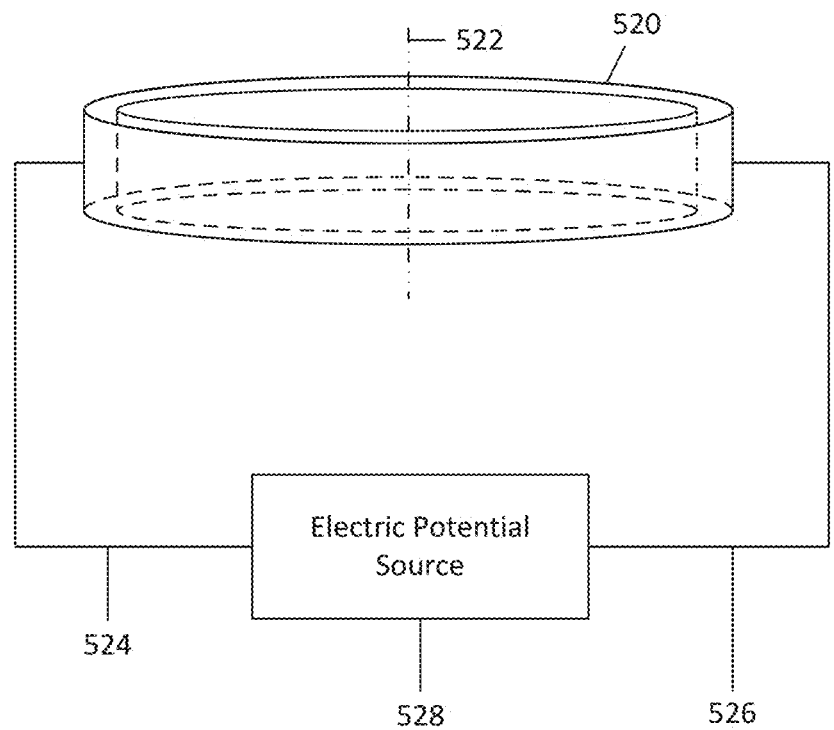
Figure 5F:
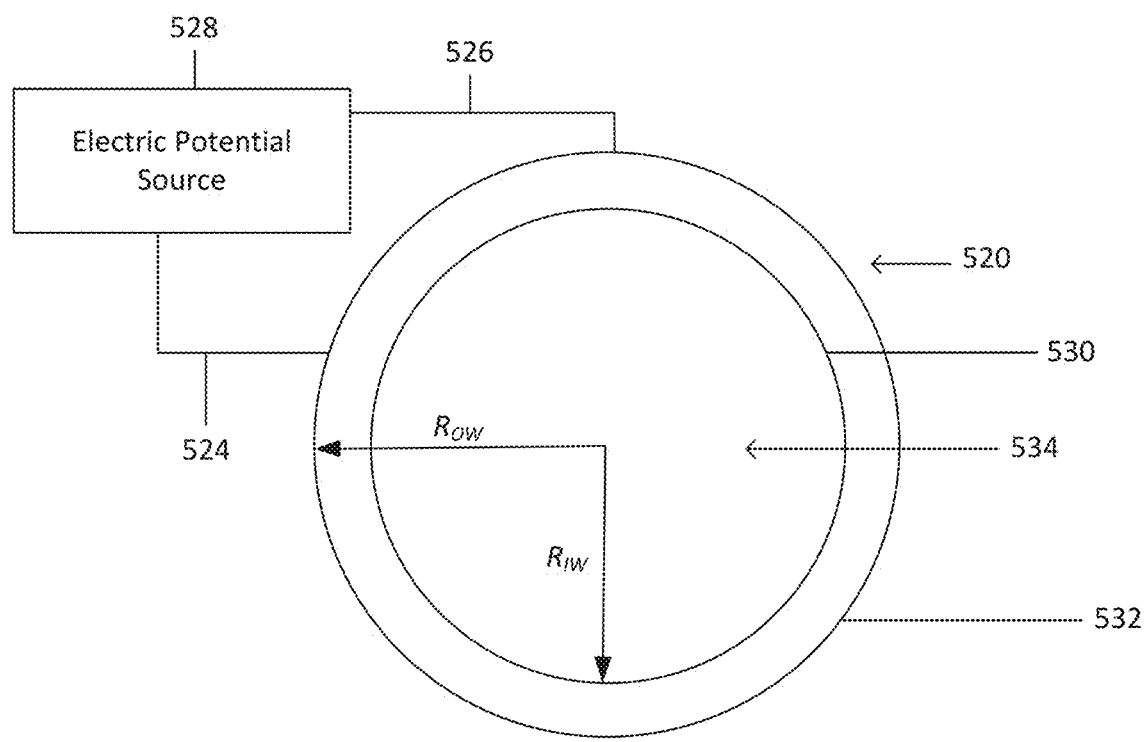

Alternatively, as shown in FIG. 5E, a sealing ring 520 may be composed of a piezoelectric material. FIG. 5F shows a top down view of the sealing ring 520. Dot-dashed line 522 represents the central or highest-symmetry axis of the sealing ring 520. The sealing ring 520 may be connected to an electric potential source 528, such as a battery, via a first lead 524 and a second lead 526. The electric potential source 528 creates a mechanical strain that causes the sealing ring 520 to tighten (i.e. sealing ring 520 radii decrease). The sealing ring 520 includes an inner wall 550, an outer wall 552, and a cavity 554. In FIG. 5F, $R_{IW}$ represents the radial distance from the center of the sealing ring 520 to the inner wall 550, and $R_{OW}$ represents the radial distance from the center of the sealing ring 520 to the outer wall 552. Alternatively, the sealing ring 520 may be in a naturally tightened stated. When applying the electric potential the sealing ring 520 expands. Alternatively, a portion of the sealing ring may be composed of the piezoelectric material, such that the piezoelectric portion acts as an actuator to cause the other portion of the sealing ring to tighten and apply the substantially uniform circumferential pressure on the primary vessel, thereby constricting the primary vessel to form the seal.

Figure 5G:
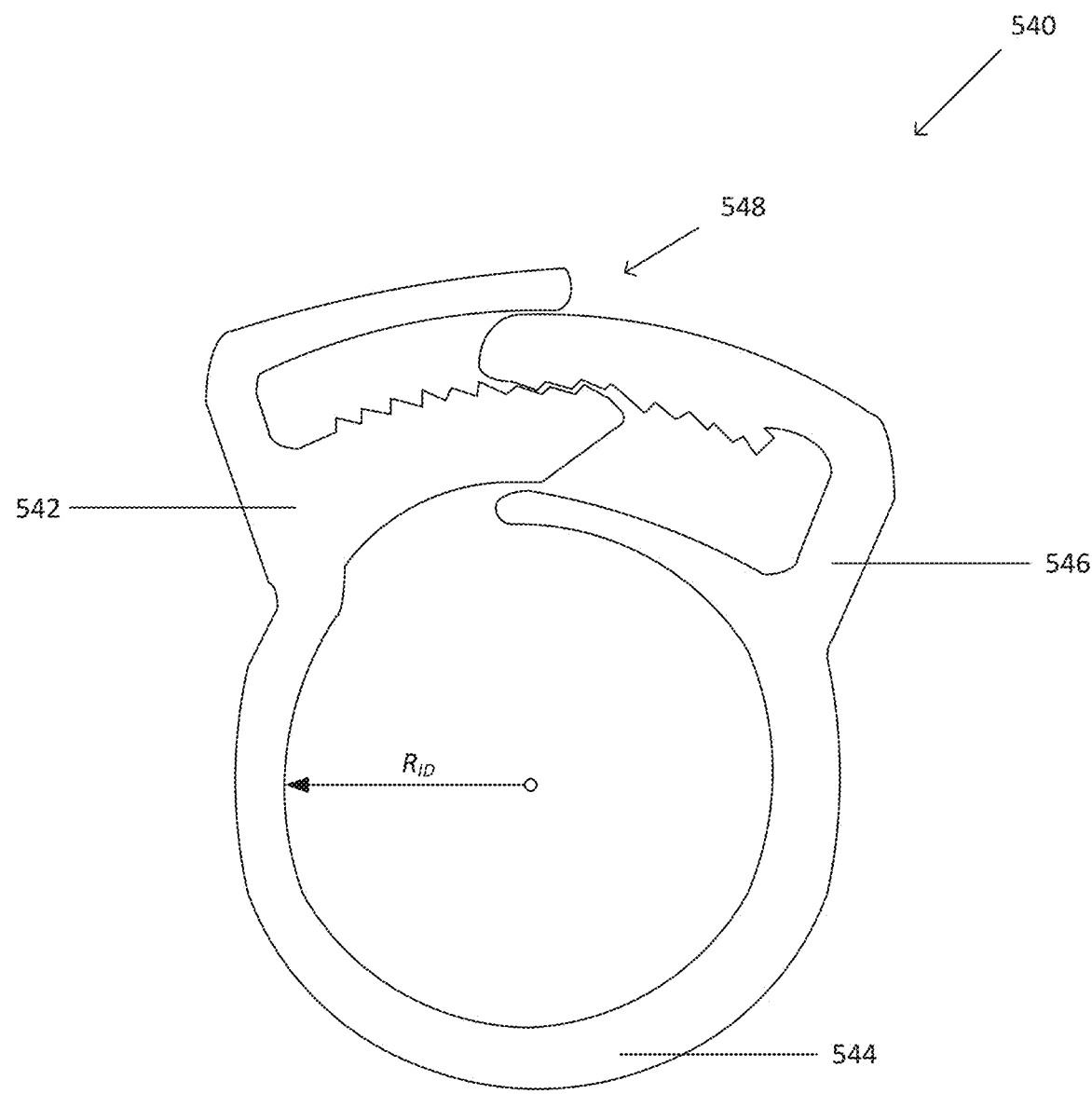

FIG. 5G shows an isometric view of a sealing ring 540. The sealing ring includes an adjustment mechanism 548 to adjust the inner diameter $R_{ID}$. The collapsible ring includes a first end 542 and a second end 546, the first and second ends 542 and 546 being joined by a band portion 544. The first and second ends 542 and 546 include complementary portions of the adjustment mechanism 548. The adjustment mechanism 548 includes, but is not limited to, a ratchet, tongue and groove, detents, or the like.

The sealing ring may also include a thermal element, such as a heated wire. The thermal element may soften the primary vessel for constriction. Alternatively, the thermal element may melt the primary vessel to provide a more adherent seal. Alternatively, the thermal element may cause the sealing ring to compress, thereby forming a seal between the primary vessel and float.

Methods

For the sake of convenience, the methods are described with reference to an example suspension of anticoagulated whole blood. But the methods described below are not intended to be so limited in their scope of application. The methods, in practice, can be used with any kind of suspension. For example, a sample suspension can be urine, blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target material can be a fraction of a sample suspension, such as buffy coat, a cell, such as ova, fetal material (such as trophoblasts, nucleated red blood cells, fetal red blood cells, fetal white blood cells, fetal DNA, fetal RNA, or the like), or a circulating tumor cell ("CTC"), a circulating endothelial cell, an immune cell (i.e. naïve or memory B cells or naïve or memory T cells), a vesicle, a liposome, a protein, a nucleic acid, a biological molecule, a naturally occurring or artificially prepared microscopic unit having an enclosed membrane, parasites (e.g. spirochetes, such as *Borrelia burgdorferi* which cause Lyme disease; malaria-inducing agents), microorganisms, viruses, or inflammatory cells. Alternatively, the sample may be a biological solid, such as tissue, that has been broken down, such as by collagenase, prior to or after being added to the primary vessel.

For example, target material enrichment is a process by which the target materials are purified relative to non-target material. For example, the target material may be enriched relative to non-target material, thereby having a ratio as low as 1 part target material, such as a single cell, protein, DNA, or the like, to 30,000,000 parts non-target material. Other ratios may include, but at not limited to, as low as approximately 1:25,000,000, 1:15,000,000, 1:10,000,000, 1:5,000,000, 1:1,000,000, 1:250,000, 1:100,000, 1:50,000, 1:25,000, 1:10,000, 1:1,000, 1:100, 1:10, or 1:1.

Furthermore, for the sake of convenience, the method is described with reference to centrifugation, such as 2 g, 5 g, 10 g, 100 g, 1000 g, 1250 g, 1500 g, 2000 g, 2500 g, 3000 g, 5000 g, or 10000 g, where g is the force of gravity. But the methods described below are not intended to be so limited in their scope of application. For example, centrifugation may not be used, and gravity (i.e. 1 g) may be used to permit the exchange of fluids and/or the separation of fluids. Alternatively, the densities of the fluids described below may be so great or the differentiation between the densities of the fluids may be so great that the separation and/or exchange of fluids occur without centrifugation. The methods, even without centrifugation, may be performed in any appropriate amount of time, including, but not limited to, less than one hour (i.e. 1 min, 5 min, 10 min, 15 min, 20 min, 30 min, 45 min, etc.), one hour (i.e. 60 min) or more than one hour (i.e. 90 min, 2 hours, 4 hours, 8 hours, 24 hours, etc.).

Furthermore, in all methods, a filling device (not shown) may be inserted into the cavity 114 of the tube 100 prior to the processing vessel 202 being inserted into the cavity 114. The filling device (not shown), such as a pump or syringe, includes a layering fluid having a density which may be less than or greater than the target material. The cannula 112 extends into the filling device (not shown) to access an inner volume at least partially filled with the layering fluid. The filling device (not shown) is used to displace or remove or substitute air within the tube with the layering fluid, such as by undergoing centrifugation or by providing a pressure gradient. The layering may have a density greater than or less than the target material. Examples of suitable layering fluids include, but are not limited to, solution of colloidal silica particles coated with polyvinylpyrrolidone (e.g. Percoll), polysaccharide solution (e.g. Ficoll), iodixanol (e.g. OptiPrep), an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

Method I

Figure 6A:
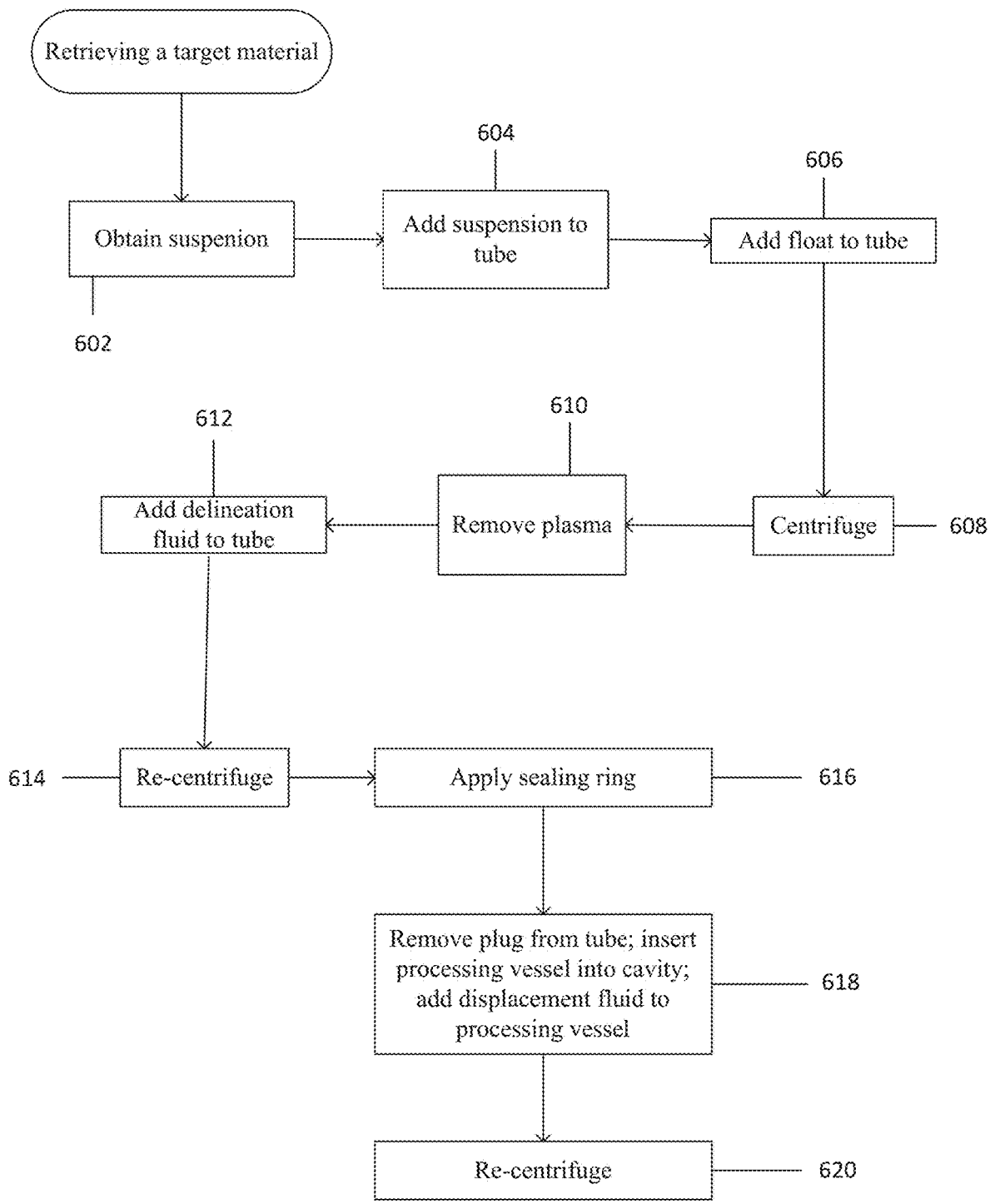
FIG. 6A shows a flow diagram of an example method for retrieving target material.
Figure 7C:
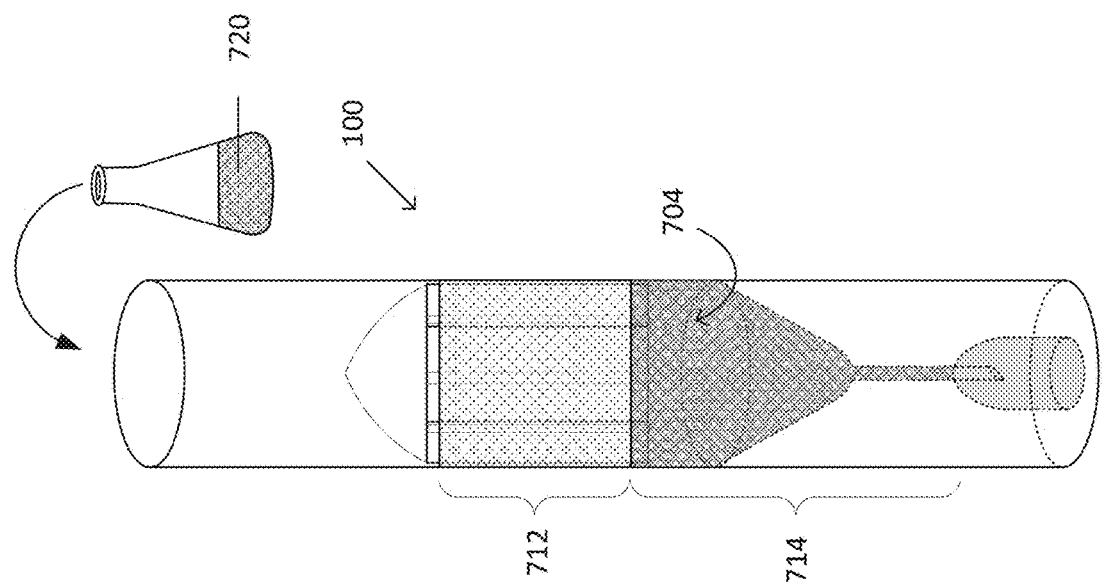
Figure 7B:
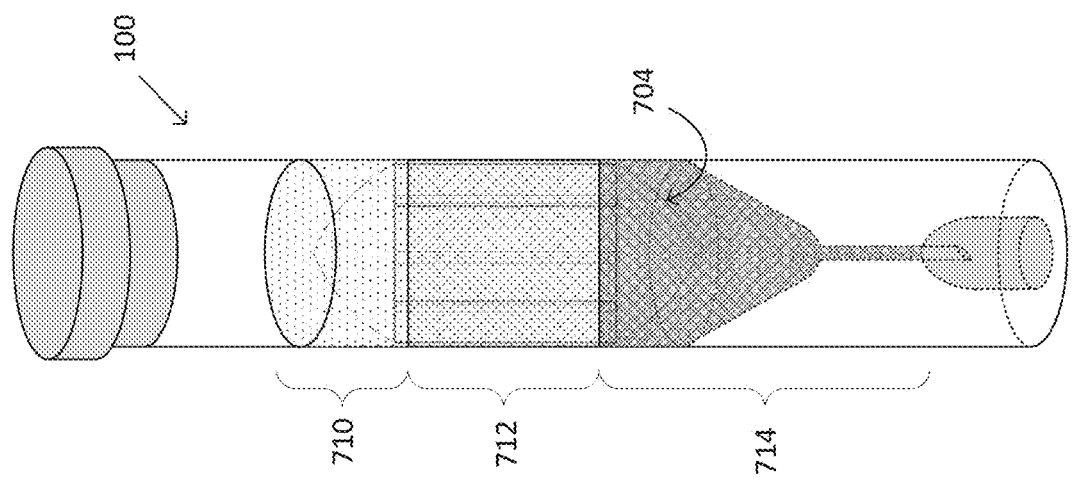
Figure 7A:
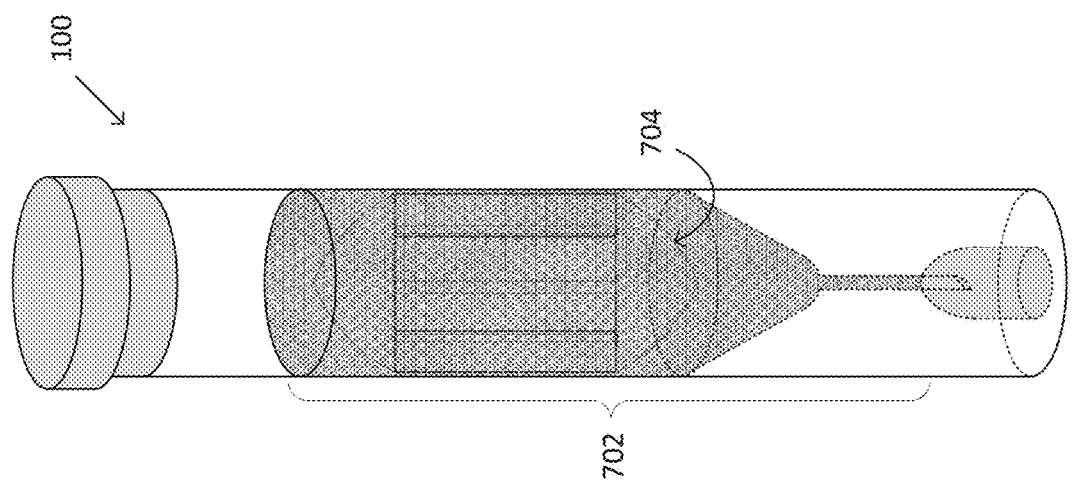

FIG. 6A shows a flow diagram for an example method for retrieving target material. In block 602, a suspension, such as anticoagulated whole blood, is obtained. In block 604, the whole blood is added to a primary vessel, such as a test tube. In block 606, a float is added to the tube. FIG. 7A shows a whole blood sample 702 and a float 704 added to the tube 100. The float 704 includes a main body, two teardrop-shaped end caps, and support members radially spaced and axially oriented on the main body. Alternatively, the float 704 may not include any support members. Alternatively, the float 704 may include support members which do not engage the inner wall of the tube 100.

In alternative embodiments, the number of support members, support member spacing, and support member thickness can each be independently varied. The support members can also be broken or segmented. The main body is sized to have an outer diameter that is less than the inner diameter of the tube 100, thereby defining fluid retention channels between the outer surface of the main body and the inner wall of the tube 100. The surfaces of the main body between the support members can be flat, curved or have another suitable geometry. The support members and the main body may be a singular structure or may be separate structures.

Embodiments include other types of geometric shapes for float end caps. The top end cap may be teardrop-shaped, dome-shaped, cone-shaped, or any other appropriate shape. The bottom end cap may be teardrop-shaped, dome-shaped, cone-shaped, or any other appropriate shape. In other embodiments, the main body of the float 504 can include a variety of different support structures for separating samples, supporting the tube wall, or directing the suspension fluid around the float during centrifugation. Embodiments are not intended to be limited to these examples. The main body may include a number of protrusions that provide support for the tube. In alternative embodiments, the number and pattern of protrusions can be varied. The main body may include a single continuous helical structure or shoulder that spirals around the main body creating a helical channel. In other embodiments, the helical shoulder can be rounded or broken or segmented to allow fluid to flow between adjacent turns of the helical shoulder. In various embodiments, the helical shoulder spacing and rib thickness can be independently varied. In another embodiment, the main body may include a support member extending radially from and circumferentially around the main body. In another embodiment, the support members may be tapered.

The float 704 can be composed of a variety of different materials including, but not limited to, metals; organic or inorganic materials; ferrous plastics; sintered metal; machined metal; plastic materials and combinations thereof. The tube 100 may have an inner wall and a first diameter. The float 704 can be captured within the tube 100 by an interference fit, such that under centrifugation, an inner wall of the tube 100 expands to permit axial movement of the float 704. When centrifugation stops, the inner wall reduces back to the first diameter to induce the interference fit. Alternatively, the inner wall may not expand and the interference fit may not occur between the float 704 and the tube 100, such that the float moves freely within the tube before, during, or after centrifugation. The end caps of the float may be manufactured as a portion of the main body, thereby being one singular structure, by machining, injection molding, additive techniques, or the like; or, the end caps may be connected to the main body by a press fit, an adhesive, a screw, any other appropriate method by which to hold at least two pieces together, or combinations thereof.

Returning to FIG. 6A, in block 608, the primary vessel, the float, and the whole blood undergo density-based separation, such as by centrifugation, thereby permitting separation of the whole blood into density-based fractions along an axial position in the tube based on density. FIG. 7B shows an isometric view of the tube 100, the float 704, and the blood having undergone density-based separation, such as by centrifugation. Suppose, for example, the centrifuged whole blood includes three fractions. For convenience sake, the three fractions include plasma, buffy coat, and red blood cells. However, when another suspension undergoes centrifugation, there may be more than, less than, or the same number of fractions, each fraction having a different density. The suspension undergoes axial separation into three fractions along the length the tube based on density, with red blood cells 714 located on the bottom, plasma 710 located on top, and buffy coat 712 located in between, as shown in FIG. 7B. The float 704 may have any appropriate density to settle within one of the fractions. The density of the float 704 can be selected so that the float 704 expands the buffy coat 712 between the main body of the float and the inner wall of the primary vessel. The buffy coat 712 can be trapped within an area between the float 704 and the primary vessel 702.

Returning to FIG. 6A, in block 610, the plasma 710 may be removed from the tube 100, such as by pipetting, suctioning, pouring, or the like. In block 612, as seen in FIG. 7C, at least one delineation fluid 720 may be added to the tube. The delineation fluid may provide further separation between the target material and any non-target material above and/or below the target material. The at least one delineation fluid 720 may have a density greater than or less than the target material. For example, when it is desirous to further separate the buffy coat 712 and the red blood cells 714, the delineation fluid may have a density greater than the buffy coat 712 and less than the red blood cells 714. The at least one delineation fluid 720 may be miscible or immiscible with the suspension fluid and inert with respect to the suspension materials. The at least one delineation fluid 720 may also provide an area in which to seal the primary vessel 702, because there is greater delineation and separation between the buffy coat 712 and the red blood cells 714. The at least one delineation fluid 720 may be used whether or not a float is used. Examples of suitable delineation fluids include, but are not limited to, solution of colloidal silica particles coated with polyvinylpyrrolidone (e.g. Percoll), polysaccharide solution (e.g. Ficoll), iodixanol (e.g. OptiPrep), cesium chloride, sucrose, sugar-based solutions, polymer-based solutions, surfactants, an organic solvent, a liquid wax, an oil, a gas, and combinations thereof; olive oil, mineral oil, silicone oil, immersion oil, mineral oil, paraffin oil, silicon oil, fluorosilicone, perfluorodecalin, perfluoroperhydrophenanthrene, perfluorooctylbromide, and combinations thereof; organic solvents such as 1,4-Dioxane, acetonitrile, ethyl acetate, tert-butanol, cyclohexanone, methylene chloride, tert-Amyl alcohol, tert-Butyl methyl ether, butyl acetate, hexanol, nitrobenzene, toluene, octanol, octane, propylene carbonate, tetramethylene sulfones, and ionic liquids; polymer-based solutions; surfactants; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane; and combinations thereof.

In block 614, the tube, float, delineation fluid, and remaining fractions undergo re-centrifugation. In block 616, a sealing ring is applied.

Figure 7D:
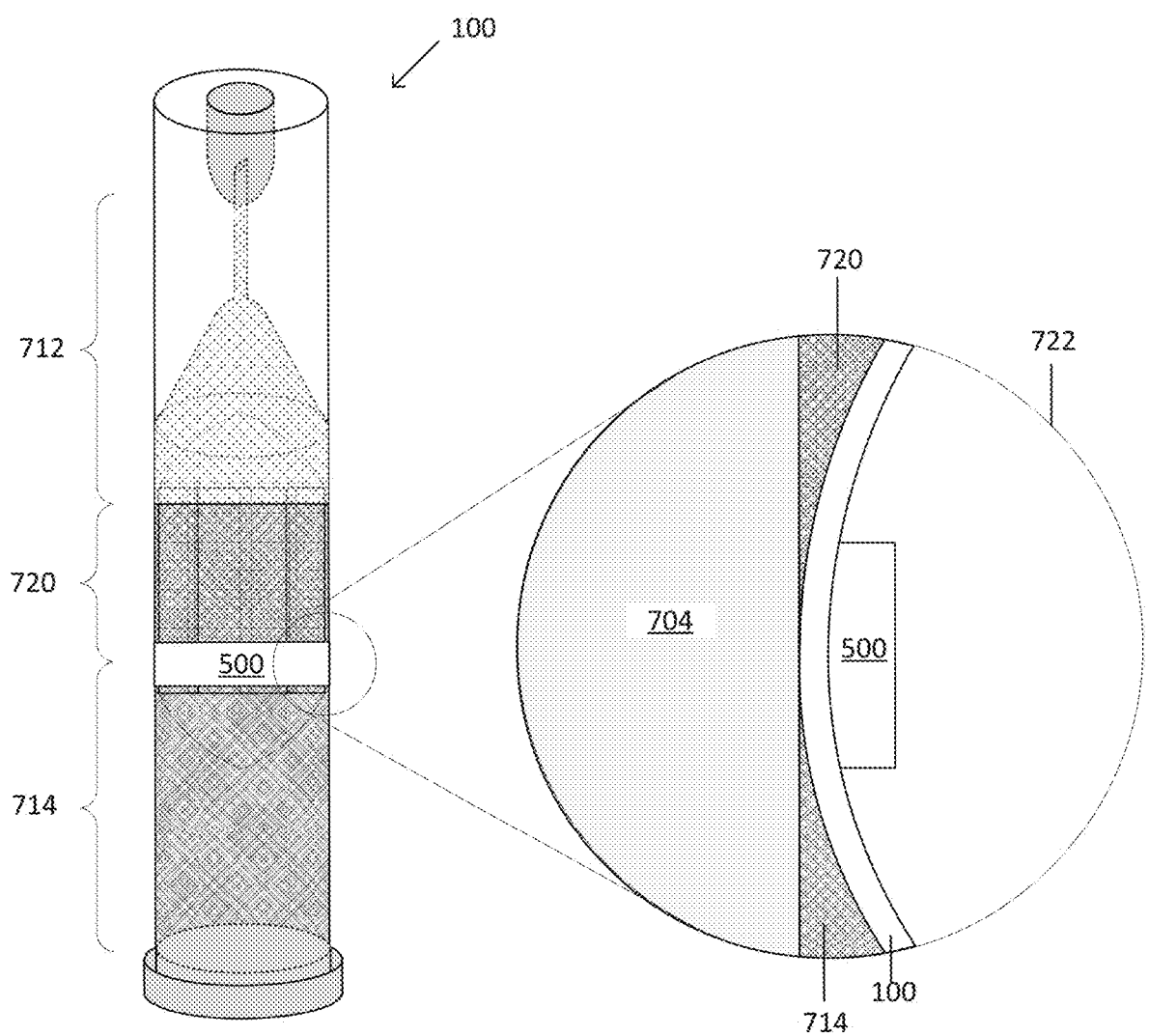

FIG. 7D shows a two-part seal including an internal pliant part to be inserted into the primary vessel and an external constricting part to constrict and deform at least the primary vessel to seal an upper portion of the primary vessel from a lower portion of the primary vessel. The external constricting part may also constrict and deform the internal pliant part. The two-part seal prevents fluids from moving past the two-part seal within the primary vessel and prevents movement of the internal pliant part. For the sake of convenience, the internal pliant part is described with reference to the float 704 and the external constricting part is described with reference to the sealing ring 500, but the system described is not intended to be so limited and may include any appropriate float and any appropriate external constricting device.

The sealing ring 500 exerts circumferential or radial forces on the tube 100, thereby causing the tube 100 to collapse inwardly against the float 704. Magnified view 722 shows the sealing ring 500 tightened around the float 704 and the tube 100. The sealing ring 500, having been placed at an interface of the delineation fluid 720 and the red blood cells 714, causes the tube 100 to collapse inwardly until a seal is formed between the tube 100 and the float 704. An outer wall of the sealing ring 500 may sit flush with an outer wall of the tube 100; the outer wall of the sealing ring 500 may extend past the outer wall of the tube 100; or, the outer wall of the tube 100 may extend past the outer wall of the sealing ring 500. The sealing ring 500 remains tightened to maintain the seal, which prevents fluids from moving past the seal in any direction. The sealing ring 500 may also remain in tension. Alternatively, the sealing ring 500 may be overtightened and then the force applied to the sealing ring 500 is removed. The sealing ring 500 may expand slightly, though still remains constricted.

To apply the sealing ring 500 and thereby form the seal, a clamp may be used to circumferentially apply a force directed toward the central axis of the tube 100 to the sealing ring 500. The sealing ring 500 is placed around the tube 100 after the tube 100 undergoes density-based separation, such as by centrifugation. The sealing ring 500 and the tube 100 are then placed into the clamp. The clamp may include a shelf to support the sealing ring 500 against the tube 100. Operation of the clamp may be automated or may be performed manually. Alternatively, the clamp may form a seal between the float 704 and tube 100 without the inclusion of the sealing ring 500. Alternatively, a seal may be formed between the float 704 and the tube 100 such as by ultrasonic welding; or by applying heat or a temperature gradient to deform and/or melt the tube 100 to the float 704. For the sake of convenience, the methods are described with reference to the sealing ring, but the methods described below are not intended to be so limited in their application and may be performed without the sealing ring.

When operation of the clamp is automated, a motor causes translation of either a collet, including collet fingers, or a pressure member to cause compression of the collet fingers. The motor may be connected to the collet or the pressure member by a shaft, such as a cam shaft, and one or more gears. A base engages and holds the object. When the collet is driven by the motor, the pressure member remains stationary. When the pressure member is driven by the motor, the collet remains stationary. The clamp may include a release, so as to cause the pressure member to slide off of the collet fingers 904, thereby removing the clamping force.

Alternatively, the clamp may be, but is not limited to, a collet clamp, an O-ring, a pipe clamp, a hose clamp, a spring clamp, a strap clamp, or a tie, such as a zip tie. The clamp may be used without a sealing ring to provide a seal between a float and a tube.

Returning to FIG. 6A, in block 618, and as seen in FIG. 7E, the tube 100 may be inverted, the plug 116 may be removed from the tube 100, the processing vessel 202 may be inserted into the tube 200, and the displacement fluid 212 may be added to the processing vessel 202. It be noted that the displacement fluid 212 may be added to the processing vessel 202 before or after inserting the processing vessel 202 into the tube 200.

Returning to FIG. 6A, in block 620, the system is then re-centrifuged. FIG. 7F shows the tube 100 and the processing vessel 202 after centrifugation. As the displacement fluid 212, having a density greater than the buffy coat 712 but less than the delineation fluid 720, flows from the processing vessel 202 into the tube 100, the buffy coat 712 moves upwards within the tube 100 through the cannula 214, and into the processing vessel 202.

The processing vessel 202 including the buffy coat 712 may then be removed from the tube 100 to undergo further processing, analysis, storage, or the like. After removing the processing vessel 202, a processing solution may be added, though the processing solution may have already been in the processing vessel prior to retrieval of the target material. The processing vessel may be shaken, such as by a vortex mixer. The processing solution (not shown), having been added before shaking either in liquid form, in a dissolvable casing, or in a breakable casing, may then mix with the buffy coat to effect a transformation and form a buffy coat-processing solution mixture. The buffy coat-processing solution mixture may then be dispensed onto a substrate, such as a microscope slide.

Method II

Figure 6B:
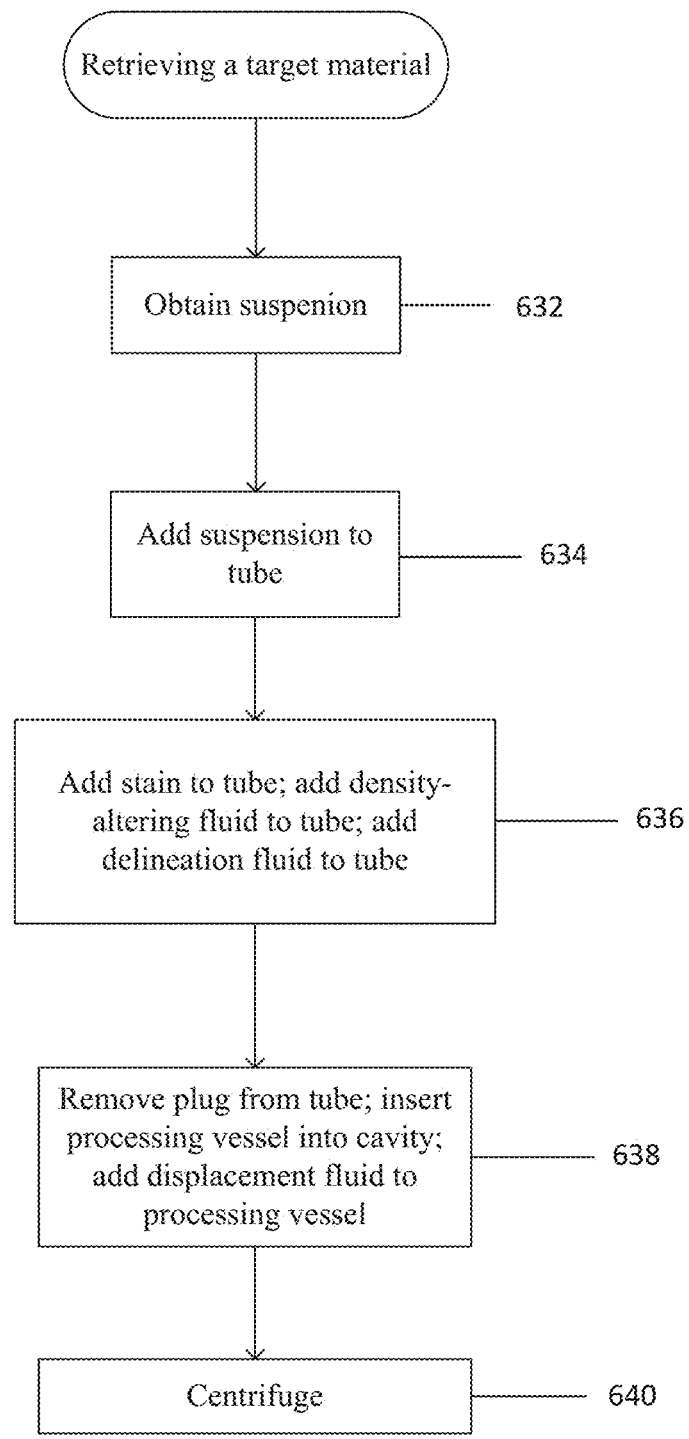
FIG. 6B shows a flow diagram of an example method for retrieving target material.
Figure 8C:
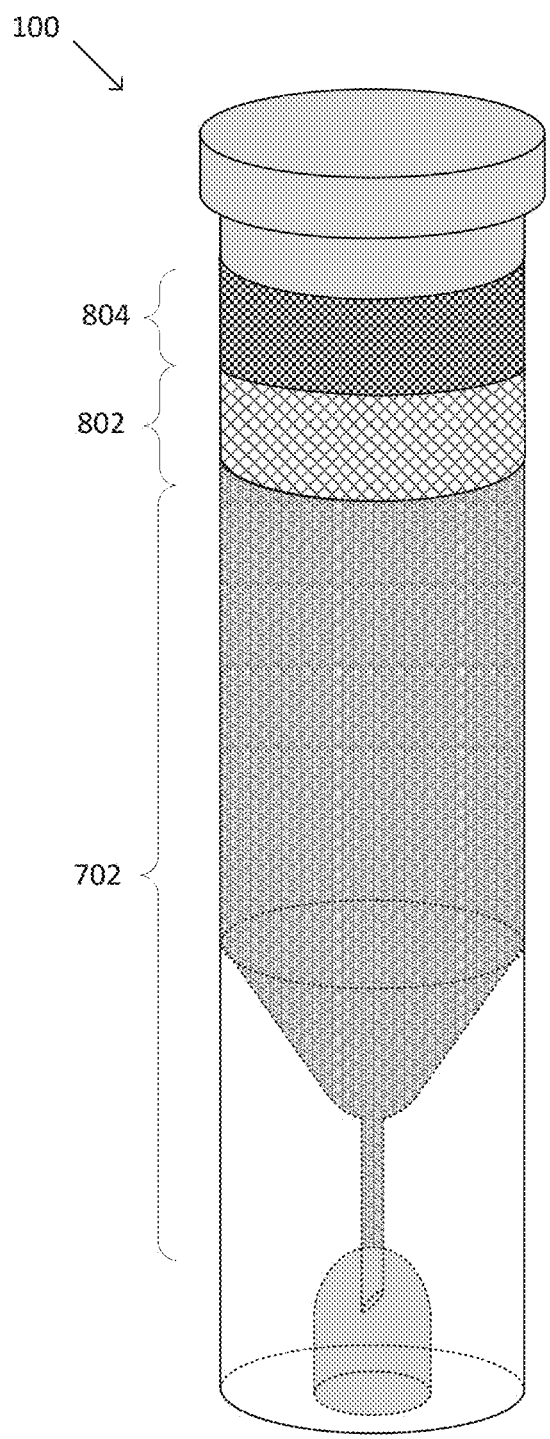

FIG. 6B shows a flow diagram for an example method for retrieving target material. In block 632, a suspension, such as anticoagulated whole blood 702, is obtained. In block 634, and as seen in FIG. 8A, the whole blood 702 is added to the tube 100. Returning to FIG. 6B, in block 636, and as seen in FIG. 8B, a stain 806, a negative enrichment reagent 804, and a delineation fluid 802 may be added to the tube 100. The stain 806 is added to the primary vessel to label the target material. The negative enrichment reagent 804 is also added to the primary vessel to change the density of a non-target material, for example, the plasma 510, without changing the density of the target material. For example, the negative enrichment reagent 804 may change the density of a non-target material such that the density of the target material is less than or greater than a changed density of the non-target material. The stain 806 and the negative enrichment reagent 804 may be allowed to incubate for any appropriate amount of time, including, but not limited to, less than one hour (i.e. 1 min, 5 min, 10 min, 15 min, 20 min, 30 min, 45 min, etc.), one hour (i.e. 60 min) or more than one hour (i.e. 90 min, 2 hours, 4 hours, 8 hours, 24 hours, etc.).

During incubation, the tube 100 may be vortexed, rocked, shaken, or any appropriate movement to enhance mixing of the stain with the target material. A stain, for example, may be a solution containing a fluorescent probe may be used to stain and thereby label the target material, thereby providing a fluorescent signal for identification and characterization. The solution containing the fluorescent probe may be added to the suspension before the suspension is added to the vessel, after the suspension is added to the vessel but before centrifugation, or after the suspension has undergone centrifugation. The fluorescent probe includes a fluorescent molecule bound to a ligand. The target material may have a number of different types of surface markers. Each type of surface marker is a molecule, such an antigen, capable of attaching a particular ligand, such as an antibody. As a result, ligands can be used to classify the target material and determine the specific type of target materials present in the suspension by conjugating ligands that attach to particular surface markers with a particular fluorescent molecule. Examples of suitable fluorescent molecules include, but are not limited to, quantum dots; commercially available dyes, such as fluorescein, FITC ("fluorescein isothiocyanate"), R-phycoerythrin ("PE"), Texas Red, allophycocyanin, Cy5, Cy7, cascade blue, Hoechst, DAPI ("4',6-diamidino-2-phenylindole") and TRITC ("tetramethylrhodamine isothiocyanate"); combinations of dyes, such as CY5PE, CY7APC, and CY7PE; and synthesized molecules, such as self-assembling nucleic acid structures. Many solutions may be used, such that each solution includes a different type of fluorescent molecule bound to a different ligand. Furthermore, a nucleus of the target material may have a different size than the nucleuses of the non-target material. Determining nuclear size may aid in differentiating between target and non-target material.

Returning to FIG. 6B, in block 638, and as seen in FIG. 8D, the tube 100 may be inverted, the plug 116 may be removed from the tube 100, the processing vessel 202 may be inserted into the tube 200, and the displacement fluid 212 may be added to the processing vessel 202. It be noted that the displacement fluid 212 may be added to the processing vessel 202 before or after inserting the processing vessel 202 into the tube 200.

Returning to FIG. 6B, in block 640, the system is then re-centrifuged. FIG. 8E shows the tube 100 and the processing vessel 202 after centrifugation. As the displacement fluid 212, having a density greater than the buffy coat 712 but less than the delineation fluid 720, flows from the processing vessel 202 into the tube 100, the buffy coat 712 moves upwards within the tube 100 through the cannula 214, and into the processing vessel 202. Furthermore, the density-alerting fluid 804, having mixed with the plasma 710 to form a high density plasma 808, causes the high density plasma 808 to have a density greater than at least the buffy coat 702 and the delineation fluid 802.

The processing vessel 202 including the buffy coat 712 may then be removed from the tube 100 to undergo further processing, analysis, storage, or the like. After removing the processing vessel 202, a processing solution may be added, though the processing solution may have already been in the processing vessel prior to retrieval of the target material. The processing vessel may be shaken, such as by a vortex mixer. The processing solution (not shown), having been added before shaking either in liquid form, in a dissolvable casing, or in a breakable casing, may then mix with the buffy coat to effect a transformation and form a buffy coat-processing solution mixture. The buffy coat-processing solution mixture may then be dispensed onto a substrate, such as a microscope slide.

Examples of suitable negative enrichment reagents include, but are not limited to, a solution of colloidal silica particles coated with polyvinylpyrrolidone (e.g. Percoll), polysaccharide solution (e.g. Ficoll), iodixanol (e.g. OptiPrep), a complex, branch glucan (e.g. Dextran), cesium chloride, sucrose, sugar-based solutions, polymer solutions, multi-phase polymer solutions, tetrameric antibody complexes (e.g. RosetteSep) or the like; or particles, such as beads (composed of at least one of a metal, silica, glass, a polymer, or the like), nanoparticles, metal-based compounds, metal complexes, lipids, sugars, or the like.

The positive enrichment reagent is also added to the primary vessel to change the density of the target material without changing the density of a non-target material. For example, the positive enrichment reagent may change the density of the target material such that the density of the non-target material is less than or greater than a changed density of the target material. The positive enrichment reagent may be allowed to incubate for any appropriate amount of time, including, but not limited to, less than one hour (i.e. 1 min, 5 min, 10 min, 15 min, 20 min, 30 min, 45 min, etc.), one hour (i.e. 60 min) or more than one hour (i.e. 90 min, 2 hours, 4 hours, 8 hours, 24 hours, etc.). Examples of suitable positive enrichment reagents include, but are not limited to, a solution of colloidal silica particles coated with polyvinylpyrrolidone (e.g. Percoll), polysaccharide solution (e.g. Ficoll), iodixanol (e.g. OptiPrep), a complex, branch glucan (e.g. Dextran), cesium chloride, sucrose, sugar-based solutions, polymer solutions, multi-phase polymer solutions, tetrameric antibody complexes (e.g. RosetteSep) or the like; or particles, such as beads (composed of at least one of a metal, silica, glass, a polymer, or the like), nanoparticles, metal-based compounds, metal complexes, lipids, sugars, or the like.

Fraction Retrieval

In one instance, it may be desirable to remove a full fraction of the blood sample to obtain the target material.

In another instance, it may be desirable to remove a portion of a fraction of the blood sample to obtain the target material. Sequential density fractionation is the division of a sample into fractions or of a fraction of a sample into sub-fractions by a step-wise or sequential process, such that each step or sequence results in the collection or separation of a different fraction or sub-fraction from the preceding and successive steps or sequences. In other words, sequential density fractionation provides individual sub-populations of a population or individual sub-sub-populations of a sub-population of a population through a series of steps. For example, buffy coat is a fraction of a whole blood sample. The buffy coat fraction can be further broken down into sub-fractions including, but not limited to, reticulocytes, granulocytes, lymphocytes/monocytes, and platelets. The buffy coat may also contain the desired target material. These sub-fractions may be obtained individually by performing sequential density fractionation.

Two or more processing vessels and respective displacement fluids may be used depending on the number of fractions or sub-fractions desired for separation and collection. Each successive displacement fluid is denser than the preceding displacement fluid. Furthermore, the displacement fluid to collect the target material has a density greater than the density of the desired target material; for example, example, the displacement fluid may have a density that is approximately 0.001 to approximately 0.005 g/cm$^3$ greater than the density of the desired target material. Similarly, each successive fraction or sub-fraction is denser than the preceding fraction or sub-fraction. Once collected, the consecutive sub-fractions may be analyzed, such as for diagnostic, prognostic, research purposes, to determine components characteristics (i.e. a complete blood count), how those characteristics change over time, or the like.

Subsequent processing vessels and displacement fluids may be used to collect additional subfractions of the buffy coat 712 until all subfractions are collected or until the desired subfraction is collected. Though sequential density fractionation is described as being performed with a float and a sealing ring, sequential density fractionation may be performed without a float, a sealing ring, or both. The following is an example method for performing sequential density fractionation after having performed all steps up to insertion of the processing vessel:

1. inserting an $(n-y)^{th}$ processing vessel into a cavity within the tube,
2. adding an $(n-y)^{th}$ displacement fluid to the $(n-y)^{th}$ processing vessel, the $(n-y)^{th}$ displacement fluid;
3. centrifuging the primary vessel and the $(n-y)^{th}$ processing vessel together, the $(n-y)^{th}$ displacement fluid to flow into the primary vessel via the tube to displace an $(n-y)^{th}$ sub-fraction of the suspension from the primary vessel into the $(n-y)^{th}$ processing vessel through the tube via the cannula;
4. removing the $(n-y)^{th}$ processing vessel including the $(n-y)^{th}$ sub-fraction from the tube.

For example, n may be any number greater than or equal to 1 and y may be any number greater than or equal to 0, such as n=2 and y=1. Furthermore, n may be the total number of sub-fractions desired and y=(n−1−number of sub-fractions already collected).

After retrieving the target material, the target material may be placed on a substrate for imaging and detection (and subsequent storage for archival purposes). At least one portion of the detected target material may then be removed from the substrate, such as by picking, to undergo further analysis. The isolated target material may be deposited into a PCR tube, a well of a well plate, a slide, or any appropriate substrate or vessel for performing the further analysis.

The target material may be analyzed using any appropriate analysis method or technique, though more specifically extracellular and intracellular analysis including intracellular protein labeling; chromogenic staining; nucleic acid analysis, including, but not limited to, DNA arrays, expression arrays, protein arrays, and DNA hybridization arrays; in situ hybridization ("ISH"—a tool for analyzing DNA and/or RNA, such as gene copy number changes); polymerase chain reaction ("PCR"); reverse transcription PCR; or branched DNA ("bDNA"—a tool for analyzing DNA and/or RNA, such as mRNA expression levels) analysis. The isolated nucleated red blood cell may undergo further processing to test for such fetal abnormalities including, but not limited to, chromosomal abnormalities (e.g. fetal aneuploidy, Down syndrome, trisomy 13, trisomy 18, or a sex chromosome abnormality, such as Turner syndrome), smaller sub-chromosomal abnormalities, gender testing, mutational analysis, and rhesus blood type testing.

These techniques may require fixation, permeabilization, and isolation of the target material prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Akt1, Akt2, c-myc, caspases, survivin, p27$^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Fibronectin, Slug, Ki-67, M30, MAGEA3, phosphorylated receptor kinases, modified histones, chromatin-associated proteins, and MAGE. To fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, enzyme-conjugated antibodies, Pap stain, Giemsa stain, or hematoxylin and eosin stain) may be used.

The density of the target material may be increased (such as by attaching a weight to the target material or by having the target material absorb or ingest the weight) or may be decreased (such as by attaching a buoy to the target material or by having the target material absorb or ingest the buoy). The weight or the buoy may be bound to a ligand. The target material may have a number of different types of surface markers. Each type of surface marker is a molecule, such as an antigen, capable of attaching a particular ligand, such as an antibody. As a result, ligands can be selected to attached specifically to the target material to alter the density of the target material. Examples of suitable weights and/or buoys include, but are not limited to beads composed of metal, glass, ceramic, plastic, or combinations thereof. Alternatively, the weight or buoy may be attached to a non-target material to change the density of the non-target material to obtain a purer sample of the target material.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents.

What is claimed is:

1. A tube comprising:
   a main body comprising a first end and a second end comprising an aperture; and
   a collection segment between the first and second ends, the collection segment comprising
      a funnel comprising a mouth proximal to the first end and an apex distal to the first end, wherein the apex of the funnel has a smaller diameter than the mouth of the funnel,
      a cavity proximal to the second end of the main body and extending from the aperture in the second end of the main body towards the apex of the funnel, and
      a cannula fluidly connecting the apex of the funnel to the cavity, the cannula extending from a hole in the apex of the funnel towards the second end of the main body and into the cavity.

2. The tube of claim 1, wherein the cannula is a tube, a needle, or a non-coring needle.

3. The tube of claim 1, further comprising a biological suspension further comprising a target material.

4. The tube of claim 1, wherein the target material is buffy coat, a cell, an ova, fetal material, a trophoblast, a nucleated red blood cell, a fetal red blood cell, a fetal white blood cell, fetal DNA, fetal RNA, a circulating tumor cell, a circulating endothelial cell, an immune cell, a vesicle, a liposome, a protein, a nucleic acid, a biological molecule, a naturally occurring microscopic unit having an enclosed membrane, an artificially prepared microscopic unit having an enclosed membrane, a parasite, a microorganism, a virus, an inflammatory cell, or a broken down biological solid.

5. The tube of claim 4, further comprising a positive enrichment reagent to change the density of the target material.

6. The tube of claim 5, wherein the suitable positive enrichment reagent is a solution of colloidal silica particles coated with polyvinylpyrrolidone, a polysaccharide solution, iodixanol, a branch glucan, cesium chloride, sucrose, a sugar-based solution, a polymer solution, a multi-phase polymer solution, a tetrameric antibody complex, a particle, a bead, a nanoparticle, a metal-based compound, a metal complex, a lipid, or a sugar.

7. The tube of claim 3, further comprising a negative enrichment reagent to change the density of a non-target material, wherein the biological suspension further comprises the non-target material.

8. The tube of claim 7, wherein the suitable negative enrichment reagent is a solution of colloidal silica particles coated with polyvinylpyrrolidone, a polysaccharide solution, iodixanol, a branch glucan, cesium chloride, sucrose, a sugar-based solution, a polymer solution, a multi-phase polymer solution, a tetrameric antibody complex, a particle, a bead, a nanoparticle, a metal-based compound, a metal complex, a lipid, or a sugar.

9. The tube of claim 1, further comprising a cap inserted within the first end.

10. The tube of claim 9, further comprising a clip placed over the cap and the first end of the tube.

11. The tube of claim 1, further comprising a float located at a longitudinal position between the first and second ends.

12. The tube of claim 11, further comprising a sealing ring located circumferentially around the main body at the same longitudinal position as at least a portion of the float.

13. The tube of claim 1, wherein the first end of the tube is a bottom end and the second end of the tube is a top end.

14. A system comprising:
   a tube comprising
      a main body comprising a first end and a second end comprising an aperture, and
      a collection segment between the first and second ends, the collection segment comprising
         a funnel comprising a mouth proximal to the first end and an apex distal to the first end, wherein the apex of the funnel has a smaller diameter than the mouth of the funnel,
         a cavity proximal to the second end of the main body and extending from the aperture in the second end of the main body towards the apex of the funnel, and
         a cannula fluidly connecting the apex of the funnel to the cavity, the cannula extending from a hole in the apex of the funnel towards the second end of the main body and into the cavity; and
   a processing vessel configured to be inserted into the cavity.

15. The system of claim 14, further comprising a displacement fluid to be added to the the processing vessel.

* * * * *